US010046091B2

(12) United States Patent
Hyde et al.

(10) Patent No.: US 10,046,091 B2
(45) Date of Patent: Aug. 14, 2018

(54) PRINTING SYSTEMS AND RELATED METHODS

(71) Applicant: Elwha LLC, Bellevue, WA (US)

(72) Inventors: Roderick A. Hyde, Redmond, WA (US); Elizabeth A. Sweeney, Seattle, WA (US); Jordin T. Kare, San Jose, CA (US)

(73) Assignee: ELWHA LLC, Bellevue, WA (US)

( * ) Notice: Subject to any disclaimer, the term of this patent is extended or adjusted under 35 U.S.C. 154(b) by 358 days.

(21) Appl. No.: 14/664,405

(22) Filed: Mar. 20, 2015

(65) Prior Publication Data

US 2016/0271367 A1 Sep. 22, 2016

(51) Int. Cl.
| | |
|---|---|
| *A61L 27/54* | (2006.01) |
| *A61L 27/38* | (2006.01) |
| *A61L 27/36* | (2006.01) |
| *A61L 27/50* | (2006.01) |
| *B29C 64/112* | (2017.01) |
| *B29C 64/386* | (2017.01) |
| *B33Y 30/00* | (2015.01) |
| *B33Y 50/02* | (2015.01) |
| *B33Y 10/00* | (2015.01) |
| *B29L 31/00* | (2006.01) |

(52) U.S. Cl.
CPC .......... *A61L 27/54* (2013.01); *A61L 27/3633* (2013.01); *A61L 27/38* (2013.01); *A61L 27/50* (2013.01); *B29C 64/112* (2017.08); *B29C 64/386* (2017.08); *B29L 2031/7532* (2013.01); *B33Y 10/00* (2014.12); *B33Y 30/00* (2014.12); *B33Y 50/02* (2014.12)

(58) Field of Classification Search
CPC ............ B29C 67/0055; B29C 67/0062; B29C 67/0051; B29C 67/0088; B29C 64/112; B29C 64/386; A61M 35/00; A61M 33/00; B41J 3/4073; B33Y 30/00; B33Y 50/02; B33Y 10/00; A61L 27/54; A61L 27/38; A61L 27/3633; A61L 27/50; B29L 2031/7532
See application file for complete search history.

(56) References Cited

U.S. PATENT DOCUMENTS

| | | | | |
|---|---|---|---|---|
| 4,249,188 | A * | 2/1981 | Graf ......................... | B41J 2/125 347/77 |
| 6,213,595 | B1 * | 4/2001 | Anagnostopoulos ...... | B41J 2/03 347/82 |
| 7,946,692 | B2 * | 5/2011 | Hawkins .................... | B41J 2/07 347/77 |

(Continued)

OTHER PUBLICATIONS

Bajaj et al."3D Biofabrication Strategies for Tissue Engineering and Regenerative Medicine" in Annu Rev Biomed Eng. Jul. 11, 2014; 16: 247-276.

(Continued)

*Primary Examiner* — David Banh
(74) *Attorney, Agent, or Firm* — Dorsey & Whitney LLP

(57) ABSTRACT

Embodiments disclosed herein related to a printing system configured to print a three-dimensional object on a region of interest. The printing system can include one or more steerable actuators that are coupled to and configured to controllably steer the one or more dispense elements. Other embodiments disclosed herein also relate to methods of using such printing systems.

42 Claims, 8 Drawing Sheets

(56) References Cited

U.S. PATENT DOCUMENTS

| | | | |
|---|---|---|---|
| 8,011,764 B2* | 9/2011 | Hawkins | F17D 1/14 347/73 |
| 8,033,811 B2 | 10/2011 | Swanson et al. | |
| 8,483,863 B1 | 7/2013 | Knox | |
| 2003/0175410 A1 | 9/2003 | Campbell et al. | |
| 2006/0119669 A1* | 6/2006 | Sharma | B41J 2/03 347/82 |
| 2010/0160183 A1 | 6/2010 | Xu et al. | |
| 2010/0258195 A1* | 10/2010 | Hawkins | F17D 1/14 137/2 |
| 2010/0258205 A1* | 10/2010 | Hawkins | B41J 2/07 137/511 |
| 2010/0259585 A1* | 10/2010 | Hawkins | B41J 2/07 347/74 |
| 2012/0212533 A1* | 8/2012 | Yoshimoto | B41J 2/04553 347/14 |
| 2012/0287186 A1* | 11/2012 | Tanaka | B41J 2/0451 347/10 |
| 2013/0017564 A1 | 1/2013 | Guillemot et al. | |
| 2013/0096708 A1* | 4/2013 | Danks | B29C 67/0088 700/98 |
| 2013/0238096 A1 | 9/2013 | Kotlus | |
| 2014/0228970 A1 | 8/2014 | Boland | |

OTHER PUBLICATIONS

Hawke, "Effects of a Thin, Flexible Nozzle on Droplet Formation and Impingement" Shane R. Hawke for the degree of Master of Science in Mechanical Engineering presented on Dec. 12, 2006, 143 pages.

Saenz, "New Skin Printer Could Print You Some New Skin" Nov. 4, 2010, 3 pages. http://singularityhub.com/2010/11/04/wake-forest-could-print-you-some-new-skin/.

Pereira et al. "Advanced biofabrication strategies for skin regeneration and repair" Nanomedicine Apr. 2013; 8(4):603-21.

Barnatt, "Bioprinting: In Situ Bioprinting", Nov. 7, 2014, 5 pages. http://www.explainingthefuture.com/bioprinting.html.

Keriquel et al., "In vivo and in situ bioprinting of cells and biomaterials to guide tissue repair" Nov. 6, 2013, 1 page. http://mymarketingteam.conference-services.net/resources/1789/3989/pdf/EORS2014_0031.pdf.

Fountain, "At the Printer, Living Tissue" Aug. 18, 2013, 5 pages. http://www.nytimes.com/2013/08/20/science/next-out-of-the-printer-living-tissue.html?pagewanted=all&_r=0.

Murphy et al. "3D bioprinting of tissues and organs" Nature Biotechnology 32, 773-785 (2014).

Ozbolat et al. "Bioprinting towards Organ Fabrication: Challenges and Future Trends" (2013) 9 pages. http://www.academia.edu/3107094/Bioprinting_towards_Organ_Fabrication_Challenges_and_Future_Trends.

Lee et al.; "Design and Printing Strategies in 3D Bioprinting of Cell-Hydrogels: A Review"; Adv. Healthcare Mater. 2016; Nov. 23, 2016; pp. 2856-2885; vol. 5, Issue 22; 2016 WILEY-VCH GmbH & Co. KGaA, Weinheim.

Ng et al.; "Skin Bioprinting: Impending Reality or Fantasy?"; Trends in Biotechnology; Sep. 2016; pp. 689-699; vol. 34, No. 9; Cell Press.

Rodriguez-Salvador et al.; "Scientometric and patentometric analyses to determine the knowledge landscape in innovative technologies: The case of 3D bioprinting"; PLOS ONE; Jun. 29, 2017; pp. 1-22; located at: https://doi.org/10.1371/journal.pone.0180375.

Tech Xplore; "Researchers develop portable 3-D skin printer to repair deep wounds"; Technology/Engineering; May 6, 2018; total of two pages; created on May 9, 2018; located at: https://techxplore.com/print444819661.html.

Zhu et al.; "3D Printed Functional and Biological Materials on Moving Freeform Surfaces"; Adv. Mater. 2018; Apr. 25, 2018; pp. 1-8; 2018 WILEY-VCH GmbH & Co. KGaA, Weinheim.

* cited by examiner

PRINTING SYSTEMS AND RELATED METHODS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

Embodiments disclosed herein are directed to printing systems configured to print a three-dimensional object on a region of interest using one or more steerable actuators that steer one or more dispense elements from which one or more materials are dispensed, and methods of using such printing systems. In an embodiment, a printing system is disclosed. The printing system includes a printing head. The printing system further includes one or more steerable actuators operably coupled to and extending from the printing head. The printing system further includes one or more dispense elements, each of which includes at least one aperture. The one or more dispense elements are operably coupled to the one or more steerable actuators. The one or more steerable actuators are configured to controllably steer the one or more dispense elements. Additionally, the one or more dispense elements are configured to controllably dispense one or more materials through the at least one aperture onto a region of interest. The printing system further includes a controller. The controller includes control electrical circuitry that is operably coupled to at least one of the printing head, the one or more dispense elements, or the one or more steerable actuators. The control electrical circuitry is configured to direct actuation of the one or more steerable actuators and dispensing of the one or more materials from the one or more dispense elements.

In an embodiment, a printing system is disclosed. The printing system includes a body-insertable device configured to be inserted into a subject to access an internal region of interest therein. The printing system further includes one or more dispense elements, each of which includes at least one aperture. The one or more dispense elements are configured to controllably dispense one or more materials through the at least one aperture onto the internal region of interest. The one or more dispense elements are at least partially positioned within the body-insertable device. The printing system further includes one or more steerable actuators operably coupled to the one or more dispense elements. The one or more steerable actuators are configured to controllably steer the one or more dispensing elements. Additionally, the printing system includes a controller. The controller includes control electrical circuitry that is operably coupled to the one or more dispense elements and the one or more steerable actuators. The control electrical circuitry is configured to direct actuation of the one or more steerable actuators and dispensing of the one or more materials from the one or more dispense elements.

In an embodiment, a method of three-dimensional printing is disclosed. The method includes, responsive to direction from control electrical circuitry, actuating one or more steerable actuators to controllably steer one or more dispense elements. The method further includes, responsive to the one or more steerable actuators controllably steering the one or more dispense elements and the direction from the control electrical circuitry, controllably dispensing one or more materials from the one or more dispense elements onto a region of interest.

Features from any of the disclosed embodiments can be used in combination with one another, without limitation. In addition, other features and advantages of the present disclosure will become apparent to those of ordinary skill in the art through consideration of the following detailed description and the accompanying drawings.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
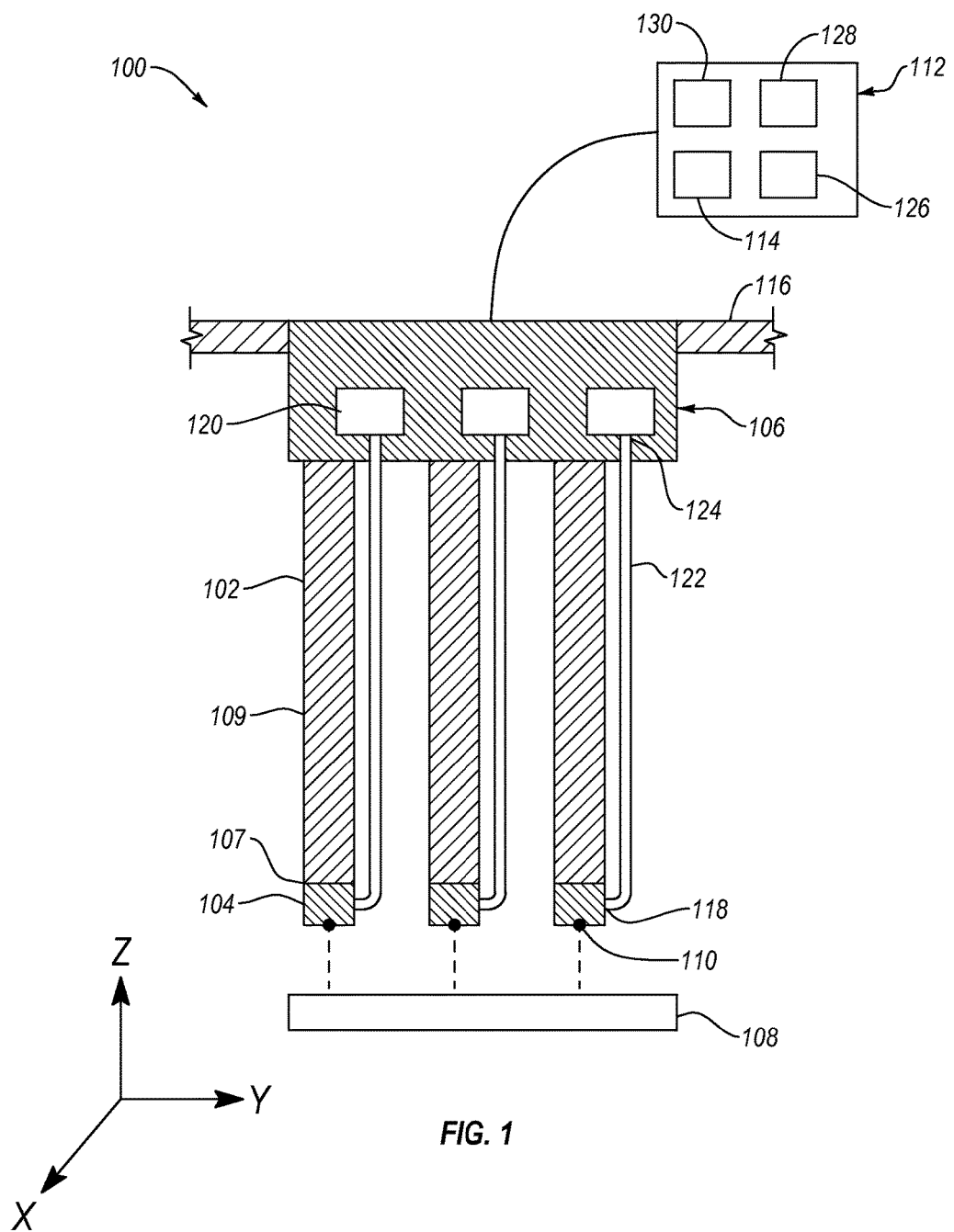
FIG. 1 is a schematic cross-sectional view of a printing system according to an embodiment.

Embodiments disclosed herein are directed to printing systems configured to print a three-dimensional object on a region of interest using one or more steerable actuators that steer one or more dispense elements from which one or more materials are dispensed, and methods of using such printing systems. The printing system can include one or more steerable actuators coupled to one or more dispense elements. The one or more steerable actuators can be configured to be controllably actuated to steer the one or more dispense elements so that the one or more dispense elements are selectively positioned adjacent to or proximate to a specific segment of a region of interest. The one or more dispense elements can controllably dispense one or more materials onto the region of interest, thereby at least partially forming the three-dimensional object. The one or more materials can include a biological material or a non-biological material. The one or more steerable actuators can be controllably steered and the one or more dispense elements can controllably dispense the one or more materials responsive to direction from control electrical circuitry of a controller. The printing system can further include a printing head configured to support at least the one or more steerable actuators.

For example, the region of interest can include a wound (e.g., a dermal wound or internal wound) and the printing system can print a scaffold and a bioink including cells and extracellular components to form a tissue graft. For example, in an orthopedic surgical intervention, the printing system can print a polymer scaffold and a bioink including osteocytes to provide a bone graft. For example, when the region of interest is an internal anatomical site, the printer can print a scaffold suitable for colonization of endogenous cells or tissues. For example, when the region of interest includes an intraabdominal site, the printing system can print all or part of an organ, (e.g., a liver), which can include vascular or microvascular structures. For example, when the internal site includes a solid tumor, the printing system can print a covering of a bioink including a hydrogel and a compound mixture including chemotherapeutics and vascular inhibitors. For example, in an intravascular procedure, the printing system can print a filler for an aneurysm. In one embodiments, the printing system is suited for printing complex patterns. For example, in a cardiovascular procedure, the printing system can print a patterned cardiac patch directly onto heart tissue, to support or repair a damaged heart, including a material having a bioink of elastic hydrogel and a second bioink comprising cardiomyocytes. For example, the printing system can print onto a region of interest that includes a substrate, biocompatible structures having complex patterns from bioinks including one or multiple structural compounds forming a scaffold and additional bioinks having cells of interest with supportive compounds. These biocompatible structures can be incubated ex vivo, e.g., for cell growth, for use in in vivo procedures. For example, in a region of interest including a weakened site on a nonorganic surface, such as a joint in a plumbing line, the printing system can print a supportive patch including an adhesive. For example, in a region of interest including a plant tissue having an abrasion, the printing system can print a plant graft to aid in healing or to introduce a heterogenous plant to form a hybrid.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented here.

FIG. 1 is a schematic cross-sectional view of a printing system 100 according to an embodiment. The printing system 100 includes one or more steerable actuators 102 configured to controllably steer one or more dispense elements 104. In the illustrated embodiment, the printing system 100 includes a printing head 106 positioned a distance above a region of interest 108. The printing head 106 includes the one or more steerable actuators 102 operably coupled to and extending therefrom towards the region of interest 108. The one or more dispense elements 104 are coupled to the one or more steerable actuators 102 such that the one or more steerable actuators 102 can controllably and selectively steer each of the one or more dispense elements 104. The one or more dispense elements 104 include at least one aperture 110 configured to dispense one or more materials onto the region of interest 108 therethrough. The printing head 106 supports components of the printing system 100. For example, the printing head 106 supports the one or more steerable actuators 102 so that the printing head 106 can maintain the one or more steerable actuators 102 above, proximate to, or adjacent to the region of interest 108. The printing head 106 can further include additional components mounted to, supported by, or at least partially enclosed by the printing head 106. The additional components can support the operation of the printing system 100, such as devices that actuate the one or more steerable actuators 102 (e.g., the pump or compressor 340 shown in FIG. 3A), hold the one or more materials (e.g., the one or more material reservoirs 120), and control the one or more steerable actuators 102 (e.g., the controller 112 shown in FIG. 3C).

The printing system 100 can further include a support structure 116 configured to support the printing head 106 a selected distance from the region of interest 108. For example, the support structure 116 can include one or more beams, columns, stretchers, or other structure that are coupled to the printing head 106 and maintain the printing head 106 the selected distance from the region of interest 108. The support structure 116 can be further configured to maintain the printing head 106 substantially stably (i.e. does not uncontrollably tilt or shift) above the region of interest 106. Stably maintaining the printing head 106 adjacent to or proximate to the region of interest 106 can improve the precision of the printing system 100 and the object to be formed. For example, the support structure 116 can include two or more beams to which the printing head 106 can be attached or rest on. In an embodiment, the support structure 116 can include a single beam to which the printing head 106 can be rigidly attached. In such an embodiment, the printing head 106 can include a clamp, pin, bracket, or other suitable attachment that rigidly attaches the printing head 106 to the support structure 116.

The printing system 100 further includes a controller 112 that is communicatively coupled to the one or more steerable actuators 102, the one or more dispense elements 104, and optionally the printing head 106. The controller 112 includes control electrical circuitry 114 configured to controllably actuate the one or more steerable actuators 102 to position the one or more dispense elements 104 adjacent to or proximate a specific segment of the region of interest 108 and to controllably dispense the one or more materials through the at least one aperture 110 towards the region of interest 108.

In an embodiment, the printing system 100 can be configured to enable the printing head 106 to move in at least one, at least two, or three dimensions. For example, portions of the support structure 116 can include means for movement, while additional portions of the support structure 116 include a track on which the potions of the support structure 116 can move. Means for movement can include, for example, a motor, gears, gravity, one or more pneumatic actuators, one or more hydraulic actuators, or other means for movement. The means for movement can move the printing head 106 from a first location remote from the region of interest 108 to a second location proximate to the region of interest 108. Additionally, in the second location, the one or more dispense elements 104 can be positioned adjacent to or proximate to the region of interest 108. The support structure 116 can move the printing head 106 from the first position to the second position responsive to a signal or direction from the control electrical circuitry 114. The support structure 116 can be configured to move from the first location to the second location without contacting the printing head 106, the one or more steerable actuators 102, or the one or more dispense elements 104 against an object. For example, the support structure 116 can include at least sensor that can detect an object and the control electrical circuitry 114 can use the data from the at least one sensor to move the printing head 106 around the object.

The support structure 116 can be configured to move the printing head 106 using a variety of techniques. In an embodiment, portions of the support structure 116 can be configured to rotate about an axis to thereby controllably tilt the printing head 106. For example, when the support structure 116 includes one shaft, the one shaft can rotate or twist, thereby tilting the printing head 106. In an embodiment, when the support structure 116 includes two shafts, one or more of the two shafts can rotate about an axis, thereby tilting the printing head 106. In an embodiment, portions of the support structure 116 can be configured to shift in at least one direction (e.g., at least one of the x-direction, y-direction, or z-direction), thereby displacing the printing head 106. For example, the support structure 116 can include two beams that are generally perpendicular to each other, where the first beam extends in the x-direction and the second beam extends in the y-direction. The first beam can be configured to move in the y-direction and the second beam can be configured to move in the x-direction. The support structure 116 can include tracks that enable the two beams to move in their respective directions. In such an embodiment, the printing head 106 can be attached to the two shafts using two or more bearings at a location about the intersection of the two beams. Such a configuration can permit the printing head 106 to be displaced along the first shaft (i.e., the x-direction) when the second shaft is moved in the x-direction, and vice-versa. Additionally, the support structure 116 can include an actuator configured to move the tracks in the z-direction, such as a hydraulic actuator. As such, the support structure 116 can move the printing head 106 in the x-direction, y-direction, and z-direction.

In an embodiment, the printing head 106 can be configured to move from the first position to the second position. For example, the printing head 106 can be attached to the support structure 116 using a bearing or other suitable attachment that enables the printing head 106 to move along the support structure 116. Additionally, the printing head 106 can include a motor attached to a wheel, a gear or a drive shaft that controllably moves the printing head 106 along the support structure 116. In an embodiment, both the support structure 116 and the printing head 106 can be configured to move the printing head 106 from the first position to the second position. For example, the support structure 116 can include one or more beams extending in the y-direction that are movable in the x-direction. The printing head 106 can configured to move along the beam in the y-direction.

In an embodiment, the printing system 100 can be configured to maintain the printing head 106 substantially stationary while the printing system 100 is printing one or more materials onto the region of interest 108. Such an embodiment can improve the stability of the printing system 100, increase controllability of the one or more steerable actuators 102, and improve the precision of printing system 100. In an embodiment, the printing head 106 can be maintained substantially stationary by the controller 112 not intentionally directing the printing head 106 or the support structure 116 to move. For example, the printing head 106 can include a motor that is powered off when it is desired for the printing head 106 or the support structure 116 to be substantially stationary. In an embodiment, the printing system 100 can include a device that prevents the printing head 106 from substantially moving during the printing process. The device can include a clamp, pin, or brake that is configured to substantially prevent the printing head 106 or the support structure 116 from moving. The device can be activated by the controller 112 prior to or when the printing system 100 dispenses the one or more materials.

In an embodiment, the printing head 106 is configured to move before, during, or after the printing system 100 dispenses the one or more materials. For example, the printing head 106 can be configured to move when the printing system 100 dispenses the one or more materials when the region of interest 108 to be printed on is larger than the printing system 100 can print without moving the printing head 106. For example, the printing system 100 can be configured to print a skin graft in a long wound in a subject or the printing system 100 can be configured to print a large three-dimensional object on a workspace. However, in such embodiments, the printing system 100 can maintain the printing head 106 substantially stationary while printing on a segment of the region of interest 108. After printing on a segment of the region of interest 108, the printing head 106 can be moved to another segment of the region of interest 108 and the deposition/printing process is repeated.

In an embodiment, the printing system 100 can include a plurality of printing heads 106. Each of the plurality of printing heads 106 can include one or more steerable actuators 102 operably coupled to and extending from the printing head 106. At least some of the plurality of printing heads 106 can be rigidly or semi-rigidly coupled together. In an embodiment, at least some of the plurality of printing heads 106 can move independently from each other 106. For example, each of the plurality of printing heads 106 can include a corresponding motor configured to move a corresponding printing head 106. In an embodiment, different portions of the support structure 116 can be attached to each of the plurality of printing heads 106. As such, when each of the different portions of the support structure 116 shifts, twists, or otherwise moves, the attached printing head 106 correspondingly moves. At least some of the plurality of printing heads 106 can be substantially similar or substantially different from each other. Some of the one or more printing heads 106 can be configured to dispense different materials, print different objects substantially simultaneously, or print different portions of the object substantially simultaneously.

The printing head 106 can support the one or more steerable actuators 102 a distance from the region of interest 108. The one or more steerable actuators 102 can be coupled to the one or more dispense elements 104 and configured to support the one or more dispense elements 104 adjacent to or proximate to the region of interest 108. The printing system 100 can include a plurality of the one or more steerable actuators 102. For example, the printing system 100 can include less than 10 steerable actuators, such as about 1 to about 3 steerable actuators, about 3 to about 5 steerable actuators, or about 5 to about 10 steerable actuators. In an embodiment, the printing system 100 can include more than 10 steerable actuators, such as 15 or more steerable actuators. The number of one or more steerable actuators 102 included in the printing system 100 can depend on the specific printing operation. Increasing the number of steerable actuators can allow for the printing system 100 to print objects formed of a plurality of materials, form more complex shapes, or print the object faster.

The one or more steerable actuators 102 can include any actuator that is configured to be controllably steered. In an embodiment, the one or more steerable actuators 102 can include a pneumatic actuator, a hydraulic actuator, a piezoelectric actuator, a shape memory material actuator, or an electroactive polymer actuator. For example, each of the one or more steerable actuators 102 can include a single actuator, an actuator coupled to another actuator, any combination of actuators, or any number of actuators. The one or more steerable actuators 102 can be steerable in one or more directions. The one or more steerable actuators 102 enables the printing system 100 to controllably steer the one or more dispense elements 104 to selectively position the one or more dispense elements 104 adjacent to or proximate a specific segment of the region of interest 108.

The one or more steerable actuators 102 can be controllably steered responsive to a direction (e.g., a signal) from the control electrical circuitry 114. In an embodiment, the control electrical circuitry 114 can directly communicate with the one or more steerable actuators 102. For example, the control electrical circuitry 114 can communicate a direction to a compressor that causes the compressor to extend or retract a piston rod of a pneumatic actuator. In an embodiment, the direction can cause a device, such as a capacitor, to induce a specific electric field that causes an electroactive polymer actuator to move responsive to the electric field. In an embodiment, the control electrical circuitry 114 can indirectly communicate with the one or more steerable actuators 102. For example, the control electrical circuitry 114 can communicate a direction to the printing head 106, which can relay the direction to the one or more steerable actuators 102.

The one or more steerable actuators 102 can be configured to be controllably steered independently of each other. For example, each of the one or more steerable actuators 102 can be configured to receive one or more directions from the control electrical circuitry 114 containing instructions for the specific steerable actuator. The specific instructions direct each of the one or more steerable actuators 102 to actuate differently. Additionally, each of the one or more steerable actuators 102 can be different. For example, the one or more steerable actuators 102 can include one steerable actuator that moves in the z-direction and a second steerable actuator moves in the x-direction or y-direction. As such, each of the two steerable actuators can be independently steerable. However, in an embodiment, at least some of the one or more steerable actuators 102 cannot move independently. For example, some of the one or more steerable actuators 102 can be rigidly or semi-rigidly attached or can receive the same direction from the control electrical circuitry 114.

In an embodiment, the one or more steerable actuators 102 can be configured to operate in one or more different environments. For example, the one or more steerable actuators 102 can be configured to operate in an in vivo environment. In such an embodiment, at least the exterior of the one or more steerable actuators can be formed of a biocompatible material. Additionally, the one or more steerable actuators can be configured to operate in a liquid since the in vivo environment can include blood or interstitial fluid. In an embodiment, the one or more steerable actuators 102 can be configured to operate in an ex vivo or in vitro environment. In an embodiment, the one or more steerable actuators 102 can be configured to print one or more materials in an adverse environment, such as in an oxidizing atmosphere. In such an embodiment, the one or more steerable actuators 102 can be formed of an oxidizing-resistant material.

In an embodiment, at least one of the one or more steerable actuators 102 or the printing head 106 can be configured to enable the one or more steerable actuators 102 to be removable and interchangeable. Such a configuration enables the printing system 100 to operate in a number of environments or dispense a number of materials without replacing the printing head 106. Similarly, such a configuration can allow damaged or less effective steerable actuators to be replaced. For example, a shape memory material actuator can suffer from "amnesia" (e.g., begins to lose its shape memory changing effect) and may need to be replaced. In an embodiment, the printing head 106 includes an interface that allows the one or more steerable actuators 102 to be reversibly attached or the printing head 106 can be configured to reversibly receive a cartridge that includes at least one of the one or more steerable actuator 102.

As previously discussed, the printing system 100 further includes the one or more dispense elements 104 coupled to the one or more steerable actuators 102. For example, each of the one or more steerable actuators 102 can be coupled to a corresponding one of the one or more dispense elements 104. The one or more dispense elements 104 can receive one or more materials via one or more inlets 118 or store the one or more materials in a material reservoir included therein. The one or more dispense elements 104 can controllably dispense the one or more materials through the at least one aperture 110 thereof onto the region of interest 108 from a position adjacent to or proximate to a specific segment of the region of interest 108. The one or more steerable actuators 102 can selectively position the one or more dispense elements 104 adjacent to or proximate to a specific segment of the region of interest 108. The one or more dispense elements 104 can controllably dispense the one or more materials responsive to the one or more steerable actuators 102 controllably steering the one or more dispense elements and direction from the control electrical circuitry 114. The one or more dispense elements 104 can be configured to be reversibly attached to the one or more steerable actuators 102, thereby enabling the one or more dispense elements 104 to be replaced.

As discussed above, each of the one or more dispense elements 104 includes the at least one aperture 110 that is configured to dispense the one or more materials therethrough. The one or more dispense elements 104 can include one or more microconduits, one or more nozzles, or one or more tubes, each of which includes the at least one aperture 110. The one or more dispense elements 104 can dispense the one or more materials using any suitable dispensing method, such as spraying the one or more materials, forming droplets of the one or more materials, or extruding the one or more materials. In an embodiment, the one or more dispense elements 104 can include disk having at least one aperture 110 therein. The size of the at least one aperture 110 can be configured to dispense the one or more materials at a specific rate or dispense a material having a certain viscosity. Additionally, the shape of the at least one aperture 110 can allow the one or more dispense elements 104 to, for example, extrude the one or more materials with a specific cross-sectional shape. The disk can further include a material configured to dispense the one or more materials. For example, the disk can be formed of a biocompatible material (e.g. stainless steel, titanium, porcelain, aluminum, or zirconium). In an embodiment, the disk can be formed of a material having a high operating temperature, thereby allowing the disk to dispense a heated material. The disk can further include a relatively stiff material that can form a droplet having a slower exit velocity (e.g., the velocity of the droplet after separating from the at least one aperture 110) than a relatively more flexible material. Additionally, the disk can include a relatively hard material, thereby allowing the disk to dispense an abrasive material, such as hard metals, ceramics, or nanoparticles.

The one or more dispense elements 104 can be configured to be heated during use. The one or more materials may need to be heated, for example, if the one or more materials are solid at room temperature, are relatively viscous at room temperature, or require heat to be effective (e.g., a material that is thermally stable at high temperatures). The one or more dispense elements 104 can include a heat source attached to, enclosed in, or incorporated into the one or more dispense elements 104. For example, electrical power can pass through portions of the one or more dispense elements 104 to provide joule heating to the one or materials to be dispensed. The one or more dispense elements 104 can include a thermal shield (not shown) that prevents or minimizes the amount of heat dissipated from the heat source to the region of interest 108.

In an embodiment, the one or more dispense elements 104 can receive the one or more materials from the one or more inlets 118 or one or more material reservoirs located therein. For example, the one or more dispense elements 104 can include only one inlet 118 or one material reservoir. In such an embodiment, the one or more dispense elements 104 can receive a single material (e.g., a mixed material). The at least one aperture 110 of the one or more dispense elements 104 can include two or more apertures to dispense the single material. Two or more apertures can allow the one or more dispense elements 104 to dispense the single material or the plurality of mixed materials at a greater rate, at multiple locations substantially simultaneously, or using a different dispense method. In an embodiment, the one or more dispense elements 104 can receive one or more materials from a plurality of inlets 118, a plurality of material reservoirs, or at least one inlet 118 and at least one material reservoir. As such, each or some of the one or more dispense elements 104 can be configured to receive two or more different materials. The one or more dispense elements 104 can include at least one aperture 110, such as a plurality of apertures 110, in which each of the plurality of apertures 110 can dispense different materials. In an embodiment, the one or more dispense elements 104 can include a single aperture that is configured to dispense the two or more materials substantially simultaneously or switch between the two or more materials such that the single aperture only dispenses one material at a time.

The one or more dispense elements 104 can be configured to operate in a number of environments. In an embodiment where the printing system 100 is configured to print a biological material, the one or more dispense elements 104 can be configured to operate in an in vivo, an ex vivo, or an in vitro environment. As such, the one or more dispense elements 104 can include a biocompatible material. The one or more dispense elements 104 can be configured to operate in a liquid. Additionally, the one or more dispense elements 104 can be configured to substantially minimize the backflow of the liquid into the one or more dispense elements 104. In an embodiment, the printing system 100 can be configured to operate in an oxidizing environment. As such, the one or more dispense elements 104 can include an oxidizing-resistant material such as around the at least one aperture 110.

The one or more dispense elements 104 can include a device that controllably dispenses the one or more materials. In an embodiment, the one or more dispense elements 104 can include a pneumatic-actuated or an electrically actuated valve that is configured to be open or closed. The valve can be opened or closed responsive to a direction received from the control electrical circuitry 114. For example, the control electrical circuitry 114 can direct the valve to limit the amount or rate that the one or more materials that are dispensed from the one or more dispense elements 104. In an embodiment, the one or more dispense elements 104 can include a pump (e.g., a micropump) that dispenses the one or more materials. In an embodiment, the one or more dispense elements 104 can include a piezoelectric material that is configured to create pressure gradients that dispense the one or more materials.

The one or more steerable actuators 102 can include an interfacial surface 107 that is remote from the printing head 106 and at least one lateral surface 109 extending from the printing head 106 to the interfacial surface 107. In the illustrated embodiment, the one or more dispense elements 104 are coupled to the interfacial surface 107 of the one or more steerable actuators 102. However, the one or more dispense elements 104 can be coupled to any location on the one or more steerable actuators 102. For example, at least one of one or more dispense elements 104 can be coupled to the at least one lateral surface 109 of one or more steerable actuators 102. In an embodiment, the one or more dispense elements 104 can be incorporated into the one or more steerable actuators 102 such that the one or more dispense elements 104 are not distinct from and integral with the one or more steerable actuators 102.

The one or more dispense elements 104 can dispense the one or more materials at a number of angles. In an embodiment, the one or more dispense elements 104 can dispense the one or more materials at an angle that is substantially perpendicular to the region of interest 108. In an embodiment, the one or more dispense elements 104 can dispense the one or more materials at any angle relative to the region of interest 108. For example, the one or more dispense elements 104 can dispense the one or more materials onto a substantially nonplanar region of interest 108. In an embodiment, the angles at which the one or more dispense elements 104 dispense the one or more materials can change as the one or more steerable actuators 102 are controllably actuated and the one or more dispense elements 104 are selectively steered at a selected angle. In an embodiment, the one or more dispense elements 104 can dispense the one or more materials at an angle that is substantially parallel or substantially non-parallel to a longitudinal axis of the one or more steerable actuators 102. In an embodiment, the one or more dispense elements 104 can include two or more apertures that are configured to dispense the one or more materials at different angles relative to each other.

The printing system 100 further includes one or more material reservoirs 120 configured to store the one or more materials. The one or more material reservoirs 120 are in fluid communication with the one or more dispense elements 104 and are configured to supply the one or more materials to the one or more dispense elements 104. For example, the one or more material reservoirs 120 can include a pump or similar device that moves or flows the one or more materials to the one or more dispense elements 104. The one or more material reservoirs 120 can be replaceable, refillable, or reusable. Additionally, the one or more material reservoirs can include one or more compartments that can be filled with the same or different materials.

The one or more material reservoirs 120 can store any of a variety of or combinations of materials. The one or more material reservoirs 120 can store non-organic materials, such as metallic materials, ceramic materials, polymeric materials, other non-organic materials. For example, the one or more material reservoirs 120 can store a functional ink, such as a conductive ink. The one or more material reservoirs 120 can store materials for use in forming biocompatible structures, microstructures, nanostructures, scaffolds, nanoscaffolds, or the like. For example, such materials include natural or synthetic polymers, polymer fibers, microfibers, nanofibers, hydrogels, thermo-responsive polymers, Matrigel™ or the like. Non-limiting examples of materials used as scaffolds in tissue engineering are described by Bajaj et al., in Annu Rev Biomed Eng. 2014 Jul. 11; 16: 247-276 (3D Biofabrication Strategies for Tissue Engineering and Regenerative Medicine), which is incorporated herein, in its entirety, by this reference. The one or more material reservoirs 120 can store organic or biological materials, such as bioinks, cells, transfected cells, peptides, proteins, carbohydrates, lipids or tissue. The biological materials can include a biomimetic. The one or more material reservoirs 120 can store materials including encapsulation materials in which materials are encapsulated, such as natural or synthetic polymers, phase change polymers, polymersomes, liposomes, or the like. The encapsulating materials can include materials stored or encapsulated therein, such as organic or nonorganic materials, compounds (e.g. medicament), or any biological material.

The biological materials used herein can include materials used to form implants, grafts, or tissues (e.g., vascularized or micro-vasculature tissue). For example, the biological material can include one or more cells including, but are not limited to, stem cells, meschenchymal cells, fibroblasts, adipocytes, pre-adipocytes, hepatocytes, osteocytes, myocytes, cardiomyocytes, smooth muscle cells, endothelial cells, epithelial cells, keratinocytes, primary cells, cultured cells, or the like. For example, the biological material can include one or more proteins including, but are not limited to, collagen, elastin, hyaluronan, fibrin, or laminin; a growth-promoting agent or any growth factor; a cytokine or chemokine; or any immune-related protein. For example, the biological material can include one or more lipids including a phospholipid, sphingolipid, or proteolipid. For example, the biological material can include one or more carbohydrates including any oligosaccharide. The one or more carbohydrates can be associated with one or more peptides, one or more proteins or one or more lipids, such as a proteoglycan, glycoprotein, glycosaminoglycan, glycolipid, or the like. For example, the one or more biomaterials can alone or together arise from, include, or form part or all of an extracellular matrix. For example, the one or more biomaterials can include a tissue, such as a tissue sphere or tissue strand, which can be included in a bioink. The one or more material reservoirs 120 can store one or more support materials that facilitate printing the one or more materials onto the region of interest 108. When the one or more materials are biological, the one or more support materials can include an inflammatory suppressant, substances that facilitate the regrowth of tissues (e.g., neurotrophin, adenosine triphosphate, vascular endothelial growth factor, or other growth factors), pain suppressant, suppressors of autoimmune factors, tissue survival promoters (e.g., anti-beta amyloid antibodies when printing neural tissue), or other similar materials. In an embodiment, the one or more support materials can include a binder, a material that supports portions of the printed object and can be removed from the object (e.g., a polymer that is burned off or vaporizes while the object densifies), an emulsifier, or a coating. For example, the one or more material reservoirs 120 can store one or more materials used to form capillaries and vascular endothelial growth factor.

In an embodiment, some of the one or more materials can be configured to operate in conjunction with each other. For example, at least one of the one or more materials can include a polymer hydrogel material configured to form a three-dimensional biocompatible scaffold when printed in the body. The biocompatible material can be stored in the one or more material reservoirs 120 and printed on the region of interest 108 by dispensing the material using the one or more dispense elements 104 that are controllably steered using the one or more steerable actuators 102. The printed biocompatible scaffold can include a porous structure. A bioink containing cells, proteins, or glycosaminoglycans may be printed onto the three-dimensional biocompatible scaffold, while the scaffold is being printed. Such a printed object can be tissue graft for repairing a tissue in vivo.

The one or more material reservoirs 120 can be formed of a material configured to stably store the one or more materials. In an embodiment, the one or more material reservoirs 120 containing one or more biological materials can be formed of a biocompatible material. In an embodiment, when the one or more materials include an abrasive material such as a ceramic material, the one or more material reservoirs 120 can be formed of materials relatively harder than the ceramic. Additionally, the one or more material reservoirs 120 can include a heat source configured to heat the one or more materials.

The one or more material reservoirs 120 can be fluidly coupled to the one or more dispense elements 104 via one or more conduits 122. The one or more conduit 122 can be coupled to an outlet 124 of the one or more material reservoirs 120 and the inlet 118 of the one or more dispense elements 104. In an embodiment, the one or more conduits 122 can include a tube. In an embodiment, the one or more conduit 122 can include a protective enclosure that protects the one or more materials, while the one or more materials move therethrough. For example, the one or more materials can include a ribbon containing the material to be printed on the region of interest 108 and the one or more conduit 122 can include a protective enclosure that isolates the ribbon from the environment. Additionally, the one or more conduits 122 can include one or more components to facilitate the flow of the one or more materials therethrough, such as a heat source or a pump.

The one or more conduits 122 can be remote from, attached to, enclosed by, or incorporated into the one or more steerable actuators 102. In an embodiment, the one or more conduit 122 can be attached to an exterior of the one or more steerable actuators 102 using a clamp or other suitable attachment. In an embodiment, the one or more steerable actuators 102 are at least partially hollow so that the one or more conduit 122 to be positioned within, defined by, or incorporated into the hollow portions of the one or more steerable actuators 102. For example, the one or more steerable actuators 102 can be formed of a hollow electroactive polymer.

The one or more material reservoirs 120 can be configured to move the one or more materials from the one or more material reservoirs 120 to the one or more dispense elements 104. For example, the one or more material reservoirs 120 can include a component, such as a pump, that moves or flows the one or more materials from the one or more material reservoirs 120. The component can operate responsive to a direction received from the control electrical circuitry 114. In an embodiment, the one or more material reservoirs 120 can be formed of a collapsible bag that exerts a compressive pressure on the one or more materials contained therein. Alternatively, the one or more material reservoirs 120 can use gravity or another component of the printing system 100 (e.g., the one or more dispense elements 104 can include a pump) to move the one or more materials. Similarly, the one or more material reservoirs 120 can include a valve that can prevent the one or more materials from leaving the one or more material reservoirs 120.

In the illustrated embodiment, the one or more material reservoirs 120 are positioned in and at least partially enclosed by the printing head 106. However, the one or more material reservoirs 120 can be positioned in other locations of the printing system 100. For example, at least some of the one or more material reservoirs 120 can be attached to an exterior of the printing head 106. In an embodiment, at least some of the one or more material reservoirs 120 can be positioned in or attached to the one or more steerable actuators 102 or the one or more dispense elements 104. In an embodiment, at least some of the one or more material reservoirs can include two or more material reservoirs coupled together (e.g., the primary material reservoir 348 and the secondary material reservoir 350). In an embodiment, at least some of the one or more material reservoirs 120 can be remote from the printing head 106, the one or more steerable actuators 102, and the one or more dispense elements 104.

The controller 112 can be communicably coupled, either directly or indirectly, to at least one of the printing head 106, the support structure 116, the one or more steerable actuators 102, the one or more dispense elements 104, or the one or more material reservoirs 120. For example, FIG. 1 illustrates that the controller 112 is communicably coupled directly to the printing head 106. The controller 112 can then be communicably coupled indirectly to other components of the printing system 100 through the printing head 106. The controller 112 can be communicably coupled through a wired or wireless (e.g., Bluetooth, Wi-Fi) connection. The controller 112 can be remote from at least one the printing head 106, the one or more steerable actuators 102, or the one or more dispense elements 104. In an embodiment, the controller 112 can at least partially be positioned within the printing head 106, the one or more steerable actuators 102, or the one or more dispense elements 104.

The controller 112 can include a user interface 126 that enables an individual to communicate with the printing system 100. The user interface 126 can include a display, mouse, keyboard, microphone, speaker, or any other device that enables an individual to communicate with the printing system 100. The user interface 126 can also include software that enables the user to communicate with the printing system 100 such as an operating system, operator controls or a process control. In an embodiment, the user interface 126 can enable an individual to input instructions or commands into the printing system 100. The commands can include build data (e.g., a CAD file), information about the one or more materials, information about one or more components of the printing system 100, instructions to execute a program, or instructions to cancel an operation. In an embodiment, the printing system 100 can send data to the user interface 126. The data can include information about the current status of the printing operation, the current status of the printing system 100, an error, or additional information. The user interface 126 can display the data.

The controller 112 can further include memory 128 storing operational instructions for operating the printing system 100. The memory 128 can include random access memory (RAM), read only memory (ROM), a hard drive, a disc (e.g., blue-ray, DVD, or compact disc), flash memory, other types of memory electrical circuitry, or other suitable memory. The instructions stored on the memory 128 can include a CAD file, a program configured to operate the printing system, information about the printing system 100 and the components thereof, information gathered by the printing system or additional information. The controller 112 can further include a processor 130 configured to direct certain operations of the printing system 100 according to the instructions contained in the memory.

As previously discussed, the controller 112 includes the control electrical circuitry 114. The control electrical circuitry 114 can be integrally formed with the memory 128 and the processor 130 of the controller 112. Alternatively, the control electrical circuitry 114 can be separate from the memory 128 and the processor 130 of the controller 112. In such an embodiment, the control electrical circuitry 114 can include its own memory and a processor.

In an embodiment, the region of interest 108 can include a substrate, a subject, an anatomical site of a subject, a plant, a test tube, a flask, a petri dish, a tissue culture dish, a portion of a partially printed object, or any workspace that the object can be printed on. For example, a substrate can be a biocompatible substrate, e.g., a substrate on which a tissue is printed ex vivo for use in an in vivo environment (e.g., an organ including a vascularized organ, a tissue, a tissue graft, a delivery depot). Such substrates can include, but are not limited to, a rigid surface, a charged surface, an inorganic surface, an organic surface, a gel surface, a polymer surface, a plastic surface, a glass surface, a printed surface, and the like. For example, the region of interest 108 can include an anatomical site in or on a subject (e.g., a mammalian subject). A site on a subject can include, for example but without limitation, a dermal site, mucosal site, or an ocular site. For example, an anatomical site of a subject can include a wound such as an abrasion, laceration, or burn, e.g., one requiring a printed treatment. For example, an anatomical site of a subject can include, but is not limited to, a tissue site (e.g., a site in need of support, repair, addition, or replacement), a surgical site, a subcutaneous site, an endodermal site, an intraperitoneal site, an intra-abdominal site, an intra-organ site, an intracranial site, a skeletal site, a muscular site, a nervous site, a cardiac site, a visceral site, a parietal site, a lumenal site, an endolumenal site. Nonlimiting examples of tissues include bone tissue, muscle tissue, visceral tissue, parietal tissue, cardiac tissue, nerve tissue, vascular tissue, dermal tissue, ocular tissue, endogenous tissue and exogenously added tissue.

In an embodiment, a user can load a CAD file of an object to be printed into the memory 128 via the user interface 126. The CAD file and any additional instructions can be stored in the memory 128. The region of interest 108 or the printing system 100 can be positioned so that the printing system 100 is proximate to the region of interest 108, and the printing system 100 can move the printing head 106 to the second position. The individual can instruct the printing system 100 to execute the printing operation through the user interface 126.

Upon receiving the instructions from the user interface 126, the control electrical circuitry 114 can communicate a direction to at least one of the one or more steerable actuators 102. The one or more steerable actuators 102 can actuate responsive to the direction, thereby selectively and controllably steering the one or more dispense elements 104. The one or more steerable actuators 102 can position the one or more dispense elements 104 adjacent to or proximate to a specific segment of the region of interest 108. The control electrical circuitry 114 can also communicate a direction instructing at least one of the one or more dispense elements 104, the one or more material reservoirs 120, or the one or more conduit 122 to prepare to disperse the one or more materials. The control electrical circuitry 114 can also communicate a direction to disperse the one or more materials onto the specific segment of the region of interest 108. For example, the direction to disperse the one or more materials can cause one or more valves to partially open or a pressure to be applied to the one or more materials. This method can be repeated until the three-dimensional object is partially or completely printed.

Figure 2:
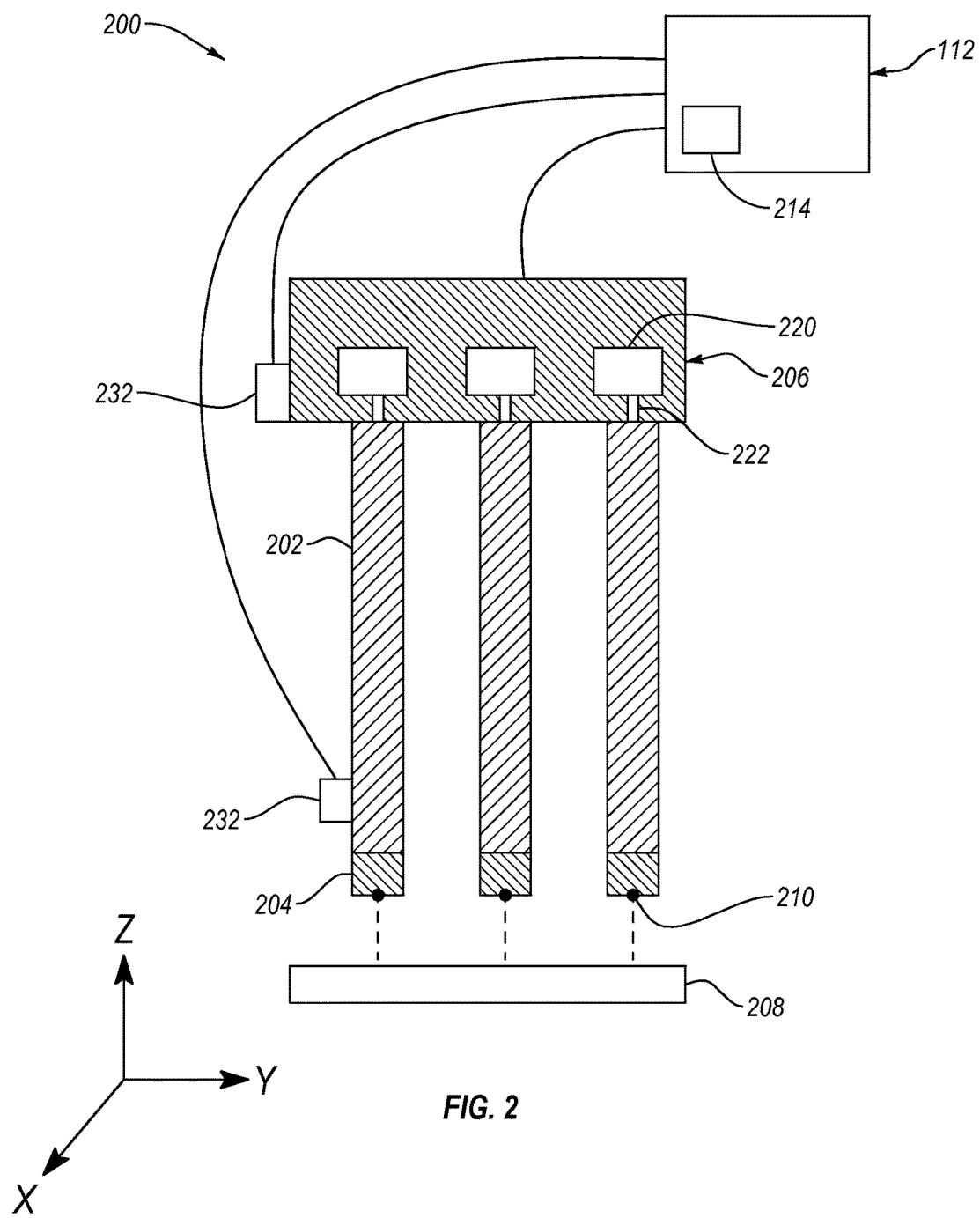
FIG. 2 is a schematic cross-sectional view of a printing system including one or more sensors according to an embodiment.

FIG. 2 is a schematic cross-sectional view of a printing system 200 including one or more sensors 232 according to an embodiment. It should be noted that the sensing principles of the printing system 200 can be employed with any of the embodiments described above for the printing system 100 shown in FIG. 1. The printing system 200 can be configured to print a three-dimensional object on a region of interest 208. The printing system 200 includes a printing head 206 coupled to and configured to support one or more steerable actuators 202. Similarly, the one or more steerable actuators 202 can be coupled to one or more dispense elements 204. The one or more steerable actuators 202 can be controllably steered to position the one or more dispense elements 204 adjacent or proximate a specific segment of the region of interest 208. The one or more dispense elements 204 can controllably dispense one or more materials from at least one aperture 210 onto the region of interest 208. Similarly, the printing system can include a controller 212. The controller 212 includes control electrical circuitry 214 configured to at least controllably steer the one or more steerable actuators 202 and controllably dispense the one or more materials from the one or more dispense elements 204.

In the illustrated embodiment, the printing system 200 includes one or more material reservoirs 220 positioned in the printing head 206. The one or more material reservoirs are coupled to the one or more dispense elements 204 through one or more conduits 222. The one or more conduits 222 are illustrated to be partially located within, defined by, or incorporated into the one or more steerable actuators 202. As such, the one or more steerable actuators 202 can be at least partially hollow. For example, the one or more steerable actuators 202 can be at least partially formed using a shape memory material actuator, an electroactive polymer actuator, or another suitable actuator.

The printing system 200 can further include one or more sensors 232 configured to detect at least one characteristic of the region of interest 208 or the printing system 200. Characteristics of the region of interest 208 sensed by the one or more sensors 232 can include the pressure, temperature, hydration, chemistry, surface contour, boundary conditions, or other features of the region of interest 208. Characteristics of the printing system 200 that can be sensed by the one or more sensors 232 can include the position of a component of the printing system 200, as a position or movement of the printing head 206 or the one or more dispense elements 204; the flow of at least one material, temperature of the printing system 200, or material to be dispensed or that has been dispensed; or other characteristics of the printing system 200. As such, the one or more sensors 232 can include a temperature sensor configured to sense temperature of the region of interest 208, a pressure sensor configured to sense pressure of the region of interest 208, a hydration sensor configured to sense moisture of the region of interest 208, a chemical sensor (e.g., an oxygen sensor or other sensor configured to sense one or more chemical elements or molecules on, in, or near the region of interest 208), a biosensor configured to sense biological matter of the region of interest 208, an optical sensor, an infrared sensor, other electromagnetic sensors (e.g., radar), a position sensor configured to sense position of the one or more dispense elements 204 or the printing head 206, an accelerometer configured to sense acceleration of the one or more dispense elements 204 or the printing head 206, a flow gauge configured to sense flow of the one or more materials dispensed from the one or more dispense elements 204, a depth sensor (e.g., depth gauge) configured to sense depth of the region of interest 208 in a subject, an acoustic sensor configured to sense amount or volume of the one or more materials dispensed onto the region of interest 208, a tilt sensor configured to sense tilting of the one or more dispense elements 204 or the printing head 206, or other suitable sensors. Some sensors can require a stimulus source that emits a stimulus the sensor detects. For example, a chemical sensor mounted to a printing system 200 can include a light source that scatters or excites chemical elements or molecules present on or near the region of interest 208 to identify the chemical elements or molecules via spectroscopy.

In an embodiment, the one or more sensors 232 can be communicably coupled to the controller 212. The controller 212 can communicate a direction directly or indirectly to at least one sensor 232 to detect a characteristic. Alternatively, the at least one sensor 232 can automatically detect the characteristic without receiving the direction. The at least one sensor 232 can detect the characteristic and send information related to the detected characteristic to the controller 212. The controller 212 can use the information to operate the printing system 100. For example, the controller 212 can request the one or more sensors 232 to detect the position and relative movement of the one or more steerable actuators 202 using a position sensor and an accelerometer. The control electrical circuitry 214 can use the detected information from the one or more sensors 232 to controllably steer or calibrate the one or more steerable actuators 202 and dispensing of the one or more materials from the one or more dispense elements 204.

In an embodiment, each of the one or more sensors 232 can communicate with each other and communicate information detected to each other. In an embodiment, two or more sensors 232 can act in tandem or in parallel. The sensing by the one or more sensors 232 can occur responsive to the information received from the other sensors 232 or responsive to direction from the control electrical circuitry 214.

In an embodiment, the one or more sensors 232 can be attached to different components of the printing system 200. For instance, a sensor can be positioned on the printing head 206, the one or more steerable actuators 202, or the one or more dispense elements 204 to be proximate the region of interest 208. The location of the one or more sensors 232 can be configured to not substantially interfere with or influence the operation of the one or more dispense elements 204 or the one or more steerable actuators 202. In an embodiment, at least one of the one or more sensors 332 can be attached to an elongated flexible member. The elongated flexible member can include a flexible dispense element such as a tube that extends from at least one of the one or more steerable actuator 202. Alternatively, the elongated flexible member can include a flexible actuator, such as an electroactive polymer actuator, or any flexible component that has at least one sensor attached thereto.

In an embodiment, at least one of the one or more sensors 232 can be replaced with a device configured to facilitate the printing process. Alternatively, the printing system 100 can include such a device configured to facilitate the printing process. For example, the printing system 100 can be configured to print an object using a light-activated resin. After printing the light-activated resin onto the region of interest 208, the device can illuminated the printed light-activated resin with a light source that exhibits a specific wavelength configured to quickly harden the light-activated resin. The device can be configured to print the light-activated resin in either a wet or dry environment.

FIGS. 3A-3D are schematic cross-sectional views of printing systems utilizing different steerable actuators, according to various embodiments. The different steerable actuators can be used with any of the embodiments illustrated and described in connection with the printing systems 100 and 200 shown in FIGS. 1 and 2. Although only a single steerable actuator and corresponding dispense element is shown in FIGS. 3A-3D, it should be understood that printing systems incorporating the steerable actuators shown in FIGS. 3A-3D can include a plurality of steerable actuators and corresponding dispense elements as disclosed in any of the embodiments illustrated and described in connection with the printing systems 100 and 200 shown in FIGS. 1 and 2. For example, the steerable actuators include a pneumatic actuator, a hydraulic actuator, a piezoelectric actuator, a shape memory material actuator, or an electroactive polymer actuator. Some or all of the foregoing actuators can be macro-scale actuators, microactuators, nanoactuators. Examples of nanoactuators include, but are not limited to, magnetic bead nanoactuators, ferroelectric switching nanoactuators, biologic-driven nanoactuators, biomemetic-driven nanoactuators, or magnetic bead nanoactuators.

Figure 3A:
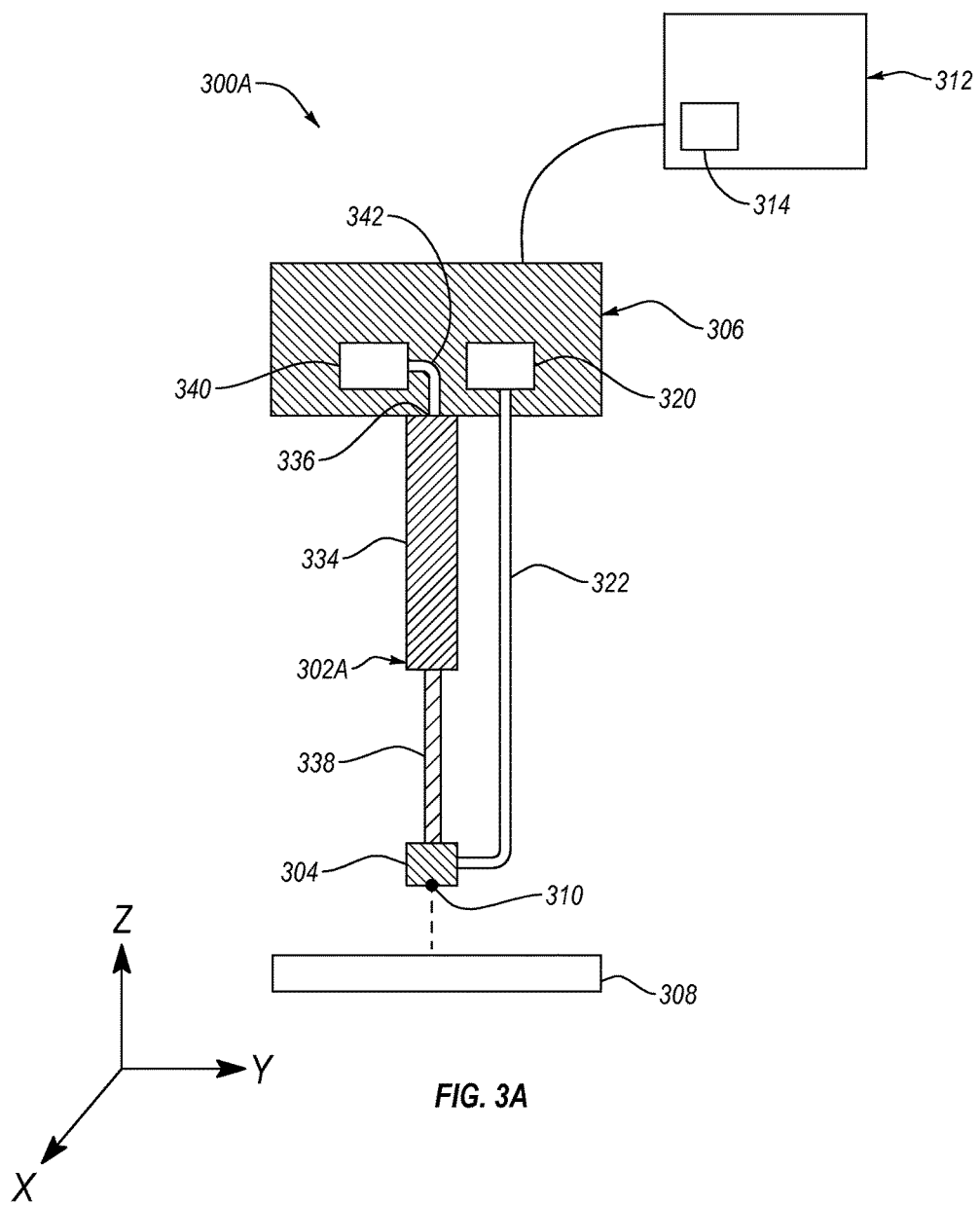
FIG. 3A is a schematic cross-sectional view of a printing system including a steerable actuator having a hydraulic or pneumatic cylinder actuator according to an embodiment.

FIG. 3A illustrates a printing system 300A including a steerable actuator 302A that is coupled to and extending from a printing head 306. The steerable actuator 302A can be controllably steered and coupled to a dispense element 304 that can controllably dispense one or more materials from at least one aperture 310 onto a region of interest 308. The printing system 300A can further include a controller 312 configured to controllably steer the steerable actuator 302A and controllably dispense the one or more materials from the dispense element 304. As such, the printing system 300A can be configured to print a three-dimensional object on the region of interest 308.

In an embodiment, the steerable actuator 302A includes a pneumatic or hydraulic actuator that controllably steers the dispense element 304 in the z-direction. In particular, the steerable actuator 302A can include a pneumatic cylinder or a hydraulic cylinder. As such, the steerable actuator 302A can include a cylinder barrel 334 configured to hold cylinder pressure. The cylinder barrel 334 can include a cap (not shown) and head (not shown) that prevents the pressure from leaking from the cylinder barrel 334. The steerable actuator can further include a piston rod 338. The cylinder barrel 334 can include a first pressurized zone that includes a pressured fluid and a second pressurized zone that does not contain a pressurized fluid. The first and second zones may be separated by a piston that is attached to the piston rod 338. The cylinder barrel 334 can further include an inlet 336 configured to allow the pressurized fluid to enter the first pressurized zone of the cylinder barrel 334. Increasing the pressure of the first pressurized zone can cause the piston rod 338 to extend and decreasing the pressure of the first pressurized zone can cause the piston rod 338 to retract. The steerable actuator 302A can further include a pump or a compressor 340 configured to move or displace a pressured liquid (e.g., a non-compressible fluid) or gas (e.g., a compressible fluid), respectively, into the first pressurized zone of the cylinder barrel 334. When the pump or compressor 340 is remote from the inlet 336, the pump or compressor 340 can be connected to the inlet 336 via an actuator conduit 342. The pump or compressor 340 can increase and decrease the pressure in the first pressure zone responsive to a direction received from the control electrical circuitry 314. The pump or compressor 340 can be configured to store some of the fluid therein or the printing system 300A may include a material reservoir configured to store some of the fluid. The dispense element 304 can be attached to the piston rod 338.

Although the described steerable actuator 302A includes a common hydraulic or pneumatic cylinder, the steerable actuator 302A can include any hydraulic or pneumatic cylinder. For example, the steerable actuator 302A can include a single action cylinder, a double action cylinder, a spring return single action cylinder, or a ram type single action cylinder. Similarly, the steerable actuator 302A can include a telescopic cylinder, a plunger cylinder, a differential cylinder, or a position sensing "smart" cylinder. The telescopic cylinder can be used when the size of the steerable actuator 302A can be limited. For example, the steerable actuator 302A can include a second steerable actuator attached to the end thereof configured to be steerable in the x-direction or the y-direction. Due to the size limitations, in an embodiment, the second steerable actuator can be a telescopic cylinder actuator. In an embodiment, the piston rod 338 can be actuated using a piezoelectric motor using stepping actions. In an embodiment, the steerable actuator 302A can be configured to rotate the dispense element 304 using a rack and pinion.

In an embodiment, the printing system 300A includes a material reservoir 320 that is coupled to the dispense element 304 through a conduit 322. Some hydraulic or pneumatic cylinders 334 can prevent the conduit 322 from being at least partially enclosed in the steerable actuator 302A. As such, the conduit 322 can extend from the material reservoir 320 to the dispense element 304, while being remote from the steerable actuator 302A. However, in an embodiment, the conduit 322 is attached to the steerable actuator 302A or the steerable actuator can be configured to partially receive the conduit 322. For example, the cylinder barrel can include a component attached thereto that is configured to at least partially enclose the conduit 322. In an embodiment, the conduit 322 may be configured to be retractable or flexible to prevent the conduit 322 from dangling.

Figure 3B:
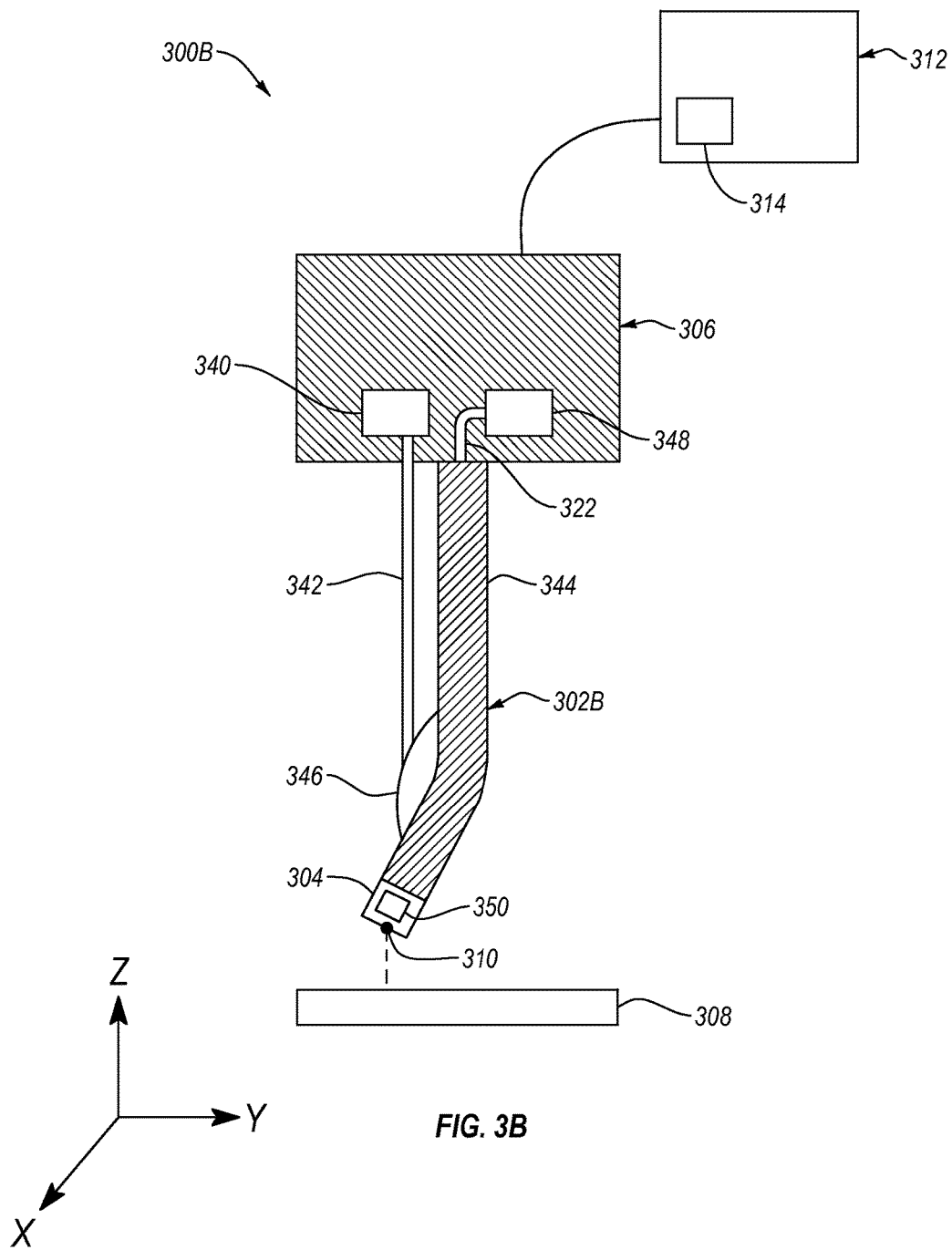
FIG. 3B is a schematic cross-sectional view of a printing system including a steerable actuator having an inflatable bubble according to an embodiment.

FIG. 3B illustrates a printing system 300B including a steerable actuator 302B being actuated in the y-direction that is coupled to and extending from a printing head 306. The steerable actuator 302B can be controllably steered and coupled to a dispense element 304. The dispense element 304 can be configured to controllably dispense one or more materials from at least one aperture 310 therein onto a region of interest 308. The printing system 300B further includes a controller 312 configured to controllably steer the steerable actuator 302B and controllably dispense the one or more materials from the dispense element 304. As such, the printing system 300B can be configured to print a three-dimensional object on the region of interest 308.

The steerable actuator 302B includes a different hydraulic or pneumatic actuator than the steerable actuator 302A illustrated in FIG. 3A. For example, the steerable actuator 302B can be a micro-hydraulic actuator or a macro-scale hydraulic or pneumatic actuator. The steerable actuator 302B can include a flexible material 344. For example, the flexible material 344 can include or be formed from silicone, polyethylene, or polyurethane. The steerable actuator 302B further includes an inflatable bubble 346 or other inflatable object attached to the exterior surface of the flexible material 344. The inflatable bubble 346 can be configured to be inflated with a pressurized fluid and should attach to the flexible material 344 in a manner that prevents the pressurized fluid from substantially leaking therefrom. Alternatively, the inflatable bubble 346 may be at least partially positioned in the flexible material 344. A pressurized fluid can be used to inflate the inflatable bubble 346 and can be provided by a pump or compressor 340. The pump or compressor 340 can be coupled to the inflatable bubble 346 using an actuator conduit 342. The actuator conduit 342 can be located remote from the flexible material 344 can be attached to or partially enclosed in the flexible material 344.

The steerable actuator 302B can be controllably steered by the control electrical circuitry 314. In an embodiment, the pump or compressor 340 can receive a direction from the control electrical circuitry 314 that can directs the pump or compressor 340 to provide a pressurized fluid (e.g., a liquid or gas such as environmental air) into the inflatable bubble 346. The pressurized fluid can cause the inflatable bubble 346 to inflate which, in turn, can cause the flexible material 344 to bend in a region proximate the inflatable bubble 346. Responsive to another direction received from the control electrical circuitry 314, the pump or compressor 340 can remove the pressurize fluid from the inflatable bubble 346, thereby deflating the inflatable bubble 346 and the returning the flexible material 344 to its resting position. In an embodiment, the pressurized fluid can be removed from the inflatable bubble using a valve or other means. The fluid used to inflate the inflatable bubble 346 can be stored is a material reservoir or in a compartment of the pump or compressor 340.

In an embodiment, the steerable actuator 302B can include a plurality of collapsible bubbles 346 attached to an exterior surface of the flexible material 344. In an embodiment, the plurality of collapsible bubbles 346 allows the steerable actuator 302B to exhibit more complex movement. In such an embodiment, the printing system 300B can include one or more pumps or compressors 340. Each of the one or more pumps or compressors 340 can be coupled to one or more of the plurality of collapsible bubbles 346 and can selectively supply a pressurized fluid to one or more of the plurality of collapsible bubbles 346 using a valve or another suitable system.

In an embodiment, the flexible material 344 can include an electroactive polymer or a shape memory material. For example, the flexible material 344 can include Nitinol, a shape memory material. The inflatable bubble 346 can be used move the flexible material 344 in a direction that the flexible material's 344 "learned" shape (e.g., the shape the flexible material 344 forms when heated or cooled) cannot accommodate, or assist the flexible material 344 move once the flexible material 344 exhibits "amnesia" (e.g., the flexible material 344 loses its memory effect after being deformed multiple times).

The printing system 300B can also include a primary material reservoir 348 and a secondary material reservoir 350. The secondary material reservoir 350 can be positioned in the dispense element 304. The primary material reservoir 348 can be coupled to the secondary material reservoir 350 using a conduit 322 that is at least partially located within, defined by, or incorporated into the hollow flexible material 344. The secondary material reservoir 350 can provide a source of the one or more materials that is more proximate the dispense element 304 than the primary material reservoir 348.

Figure 3C:
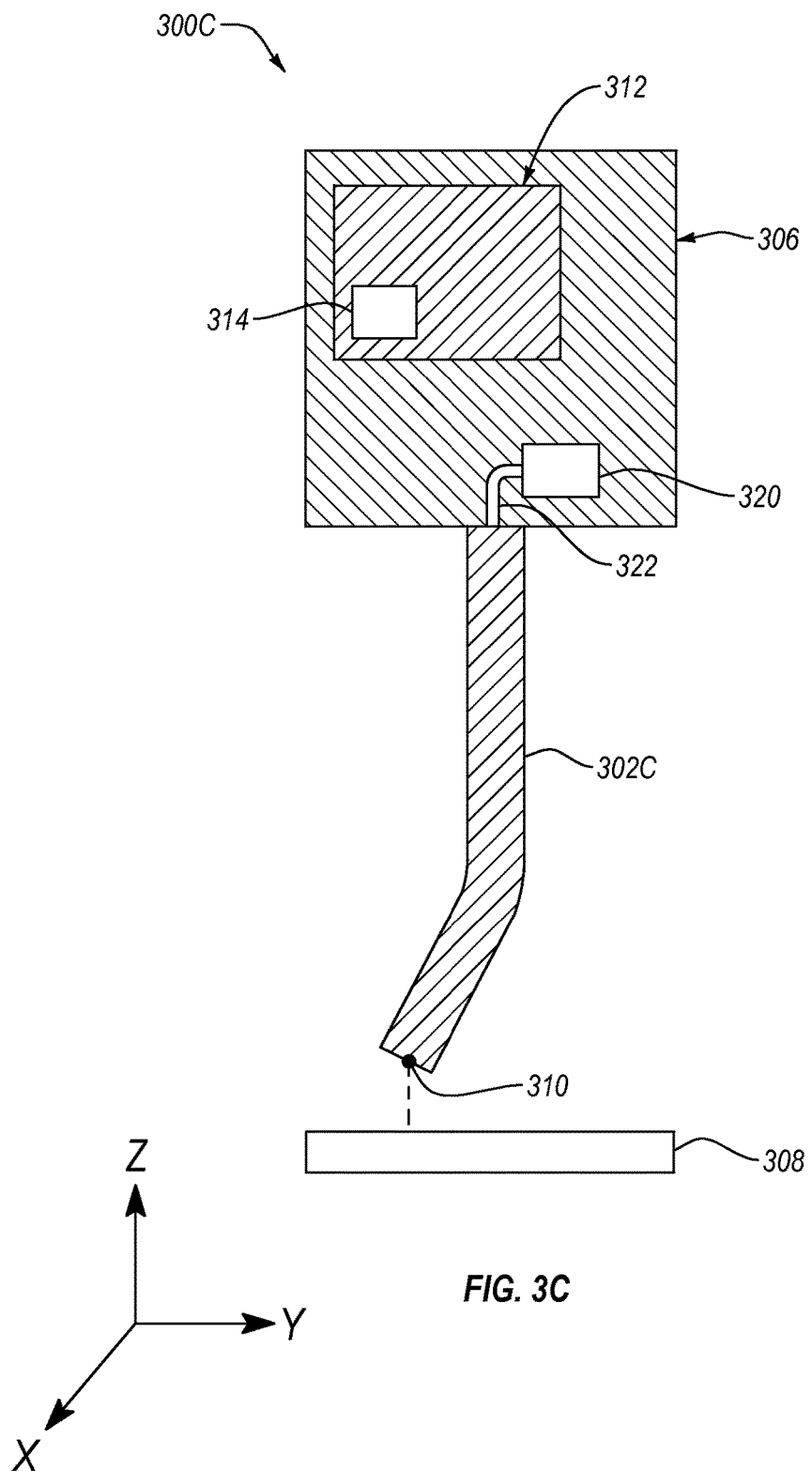
FIG. 3C is a schematic cross-sectional view of a printing system including a steerable actuator according to an embodiment.

FIG. 3C illustrates a printing system 300C including a steerable actuator 302C being actuated in the y-direction that is coupled to and extending from a printing head 306. The steerable actuator 302C can be controllably steered and configured to controllably dispense one or more materials onto a region of interest 308. The printing system 300C can further include a controller 312 configured to controllably steer the steerable actuator 302C and controllably dispense the one or more materials. The controller 312 can be at least partially located within the printing head 306. As such, the printing system 300C can be configured to print a three-dimensional object on the region of interest 308.

In the illustrated embodiment, the steerable actuator 302C includes a material that moves responsive to an applied energy. The applied energy can be provided by a direction from the control electrical circuitry 314 or the direction can instruct another component to supply the applied energy source. In an embodiment, the steerable actuator 302C includes an electroactive polymer actuator. The electroactive polymer can change shape or size when an electric field is applied thereby allowing the steerable actuator 302C to be controllably steered. The electric field can be applied using any device or method capable of applying an electric field to the electroactive polymer, such as a capacitor, a magnet, a voltage source, or a coil of wires. For example, the steerable actuator 302C can include an ionic polymer-metal composite. An electric field can be applied to the ionic polymer-metal composite by an electrode coating on the steerable actuator 302C. The electric field causes the cations in the ionic polymer-metal composite to redistribute to balance the charge, thereby causing the negatively charged portions of the polymer to swell. Other examples of electroactive polymer actuators include dielectric electroactive polymers, ferroelectric polymers (e.g., polyvinylidene fluoride), electrostrictive graft polymers, liquid crystalline polymers, ionic electroactive polymers (e.g., electroactive polymer gels, ionic polymer-metal composites), non-ionic electroactive polymers, carbon nanotube actuators, conductive polymers (e.g., polypyrrole, polyaniline, poly(3,4-ethylenedioxythiophene), or poly(3,4-ethylenedioxypyrrole)) electrorheological fluids, electroactive polymer gels, or other electroactive polymers. A polymer can also that controllably deforms in a specific environment. For example, the steerable actuator 302C can include a collagen filament that swells when exposed to an acid or alkali solution.

In an embodiment, the steerable actuator 302C includes a piezoelectric actuator. For example, the piezoelectric actuator can be a microactuator. The piezoelectric actuator can controllably deform when an electric field is applied to the steerable actuator 302C, thereby allowing the steerable actuator 302C to be controllably steered. For example, the steerable actuator can include lead zirconate titanate crystals. The lead zirconate titanate crystals can deform by about 0.1% of its original dimension when an electrical field is applied thereto. As such, the steerable actuator 302C including lead zirconate titanate can be used when a precision printing process is required. For example, the steerable actuator 302C including lead zirconate titanate can have better that micrometer precision. Other piezoelectric materials can exhibit improved precision or larger deformations than lead zirconate titanate.

In an embodiment, the steerable actuator 302C includes a shape memory material actuator. The shape memory material actuator can controllably deform when exposed to high or low temperatures. For example, the steerable actuator 302C can include a shape memory material that exhibits a two way memory effect. As such, the steerable actuator 302C can be configured to have "learned" a first memory effect (i.e. deformation) when exposed to high temperatures and a second memory effect when exposed to low temperatures. The steerable actuator 302C can include one or more thermal devices configured to apply a high or low temperature to the steerable actuator 302C. The one or more thermal devices can include a heat source or a high thermally conductive material that removes heat from the steerable actuator 302C. The control electrical circuitry 314 may use to one or more thermal devices to controllably steer the steerable actuator 302C into its first memory effect or second memory effect. The movements of the steerable actuator can be further controlled by only exposing portions of the steerable actuator 302C to the high or low temperature. Additionally, the rate of deformation of the steerable actuator 302C can be controlled by the specific temperature applied to the steerable actuator 302C. The shape memory material actuator can include a material exhibiting a one-way memory effect or a two-way memory effect. Also, the shape memory material can be formed of any shape memory alloy, such as copper-aluminum-nickel alloys, copper-zinc-aluminum alloys, nickel-titanium alloys, iron-manganese-silicon alloys, or other shape memory material.

In the illustrated embodiment, the steerable actuator 302C includes a dispense element incorporated therein. For example, the steerable actuator 302C can include at least one aperture 310 configured to dispense the one or more materials. Additionally, the steerable actuator 302C can be substantially hollow. In such an embodiment, a conduit 322 can extend between the material reservoir 320 and aperture 310.

Figure 3D:
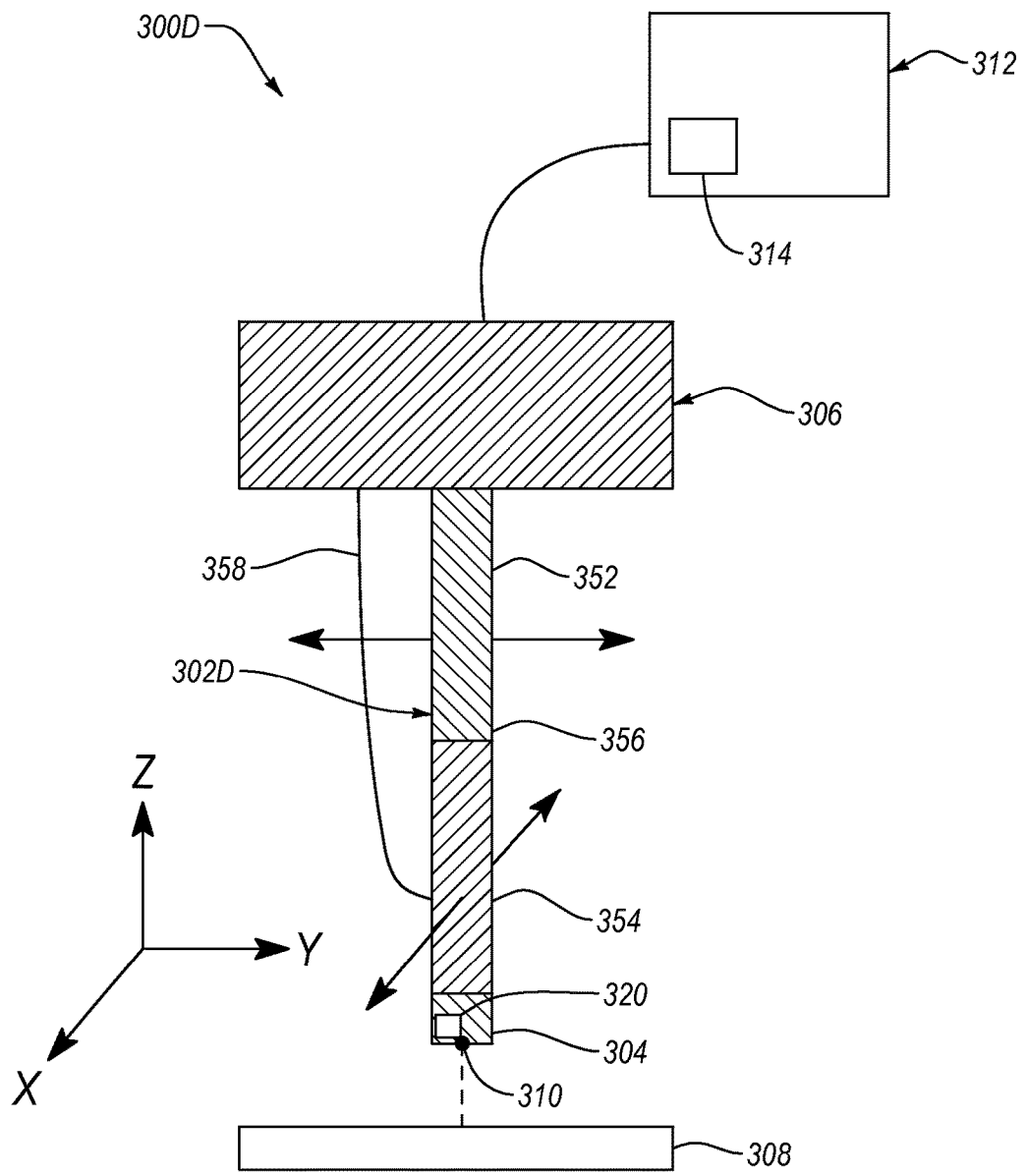
FIG. 3D is a schematic cross-sectional view of a printing system including a steerable actuator having two actuators according to an embodiment.

FIG. 3D illustrates a printing system 300D including a steerable actuator 302D that includes two or more actuators in an embodiment. The steerable actuator 302D can be coupled to and supported by the printing head 306. Additionally, the steerable actuator 302D can include a dispense element 304 coupled thereto. The steerable actuator 302D can be configured to controllably steer the dispense element 304 responsive to direction from the controller 312. The dispense element 304 can be configured to controllably dispense one or more materials from at least one aperture 310 responsive from one or more directions from the controller 312. The material reservoir 320 can store the one or more materials and can be positioned within the dispense element 304. Therefore, the printing system 300D can be configured to print an object on a region of interest 308.

In the illustrated embodiment, the steerable actuator 302D includes a first actuator 352 and a second actuator 354. However, the steerable actuator 302D can include more than two actuators. The steerable actuator 302D formed using two or more actuators can increase a number of directions the steerable actuator can move (e.g., two or more directions or three directions (x-, y-, and z-directions), increase the complexity of the movement, improve the control of the printing system 300D, improve the precision of the printing system 300D (e.g., include a piezoelectric actuator), or improve the distance the steerable actuator 302D can actuate.

In an embodiment, the first actuator 352 can include an electroactive polymer actuator configured to move in the y-direction and the second actuator 354 can include an electroactive polymer actuator configured to move in the x-direction. While the first actuator 352 and the second actuator 354 are described as being electroactive polymer actuators, that the first actuator 352 and the second actuator 354 can include any actuator. The first actuator 352 and the second actuator 354 can be attached together at an interface 356. The interface 356 can be configured to allow the second actuator 354 to be interchangeable.

In an embodiment, electric fields can be applied to the first actuator 352 and the second actuator 354 responsive to direction from the control electrical circuitry 314. A wire 358 can supply electrical energy used to apply an electric field to the second actuator 354 since the second actuator 354 is remote from the printing head 306. The first actuator 352 and the second actuator 354 can be controllably steered independently of each other. For example, a first direction from the control electrical circuitry 314 can cause a first electric field to be applied to the first actuator 352 thereby controllably steering the first actuator 352. Similarly, a second direction from the control electrical circuitry 314 can cause a second electric field to be applied to the second actuator 354 thereby controllably steering the second actuator 354. As such, the steerable actuator 302D can be controllably steered in the x-direction, the y-direction, or the z-direction.

Figure 4A:
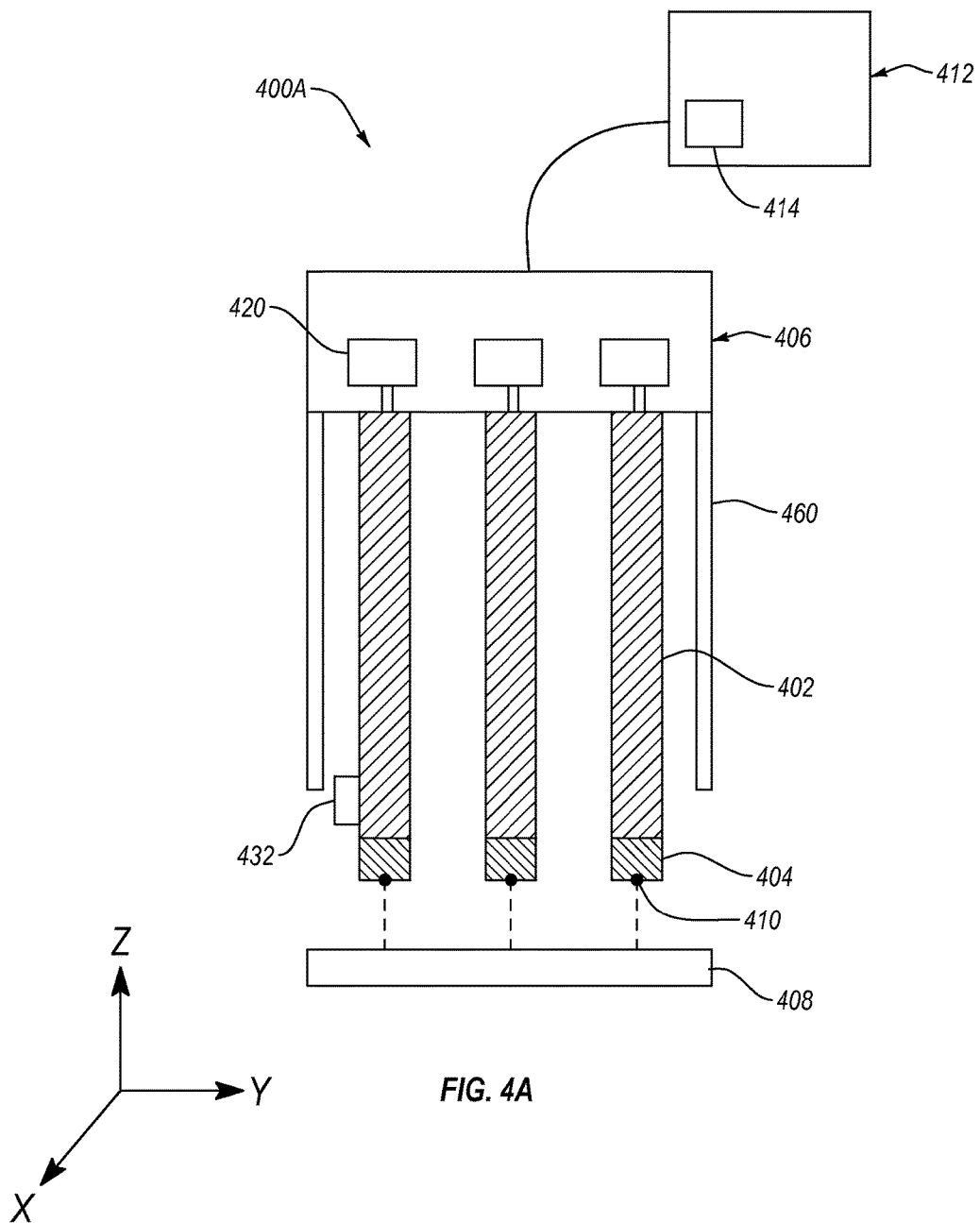
FIG. 4A is a schematic cross-sectional view of a printing system that is configured to be partially inserted into an internal region of interest of a subject according to an embodiment.
Figure 4B:
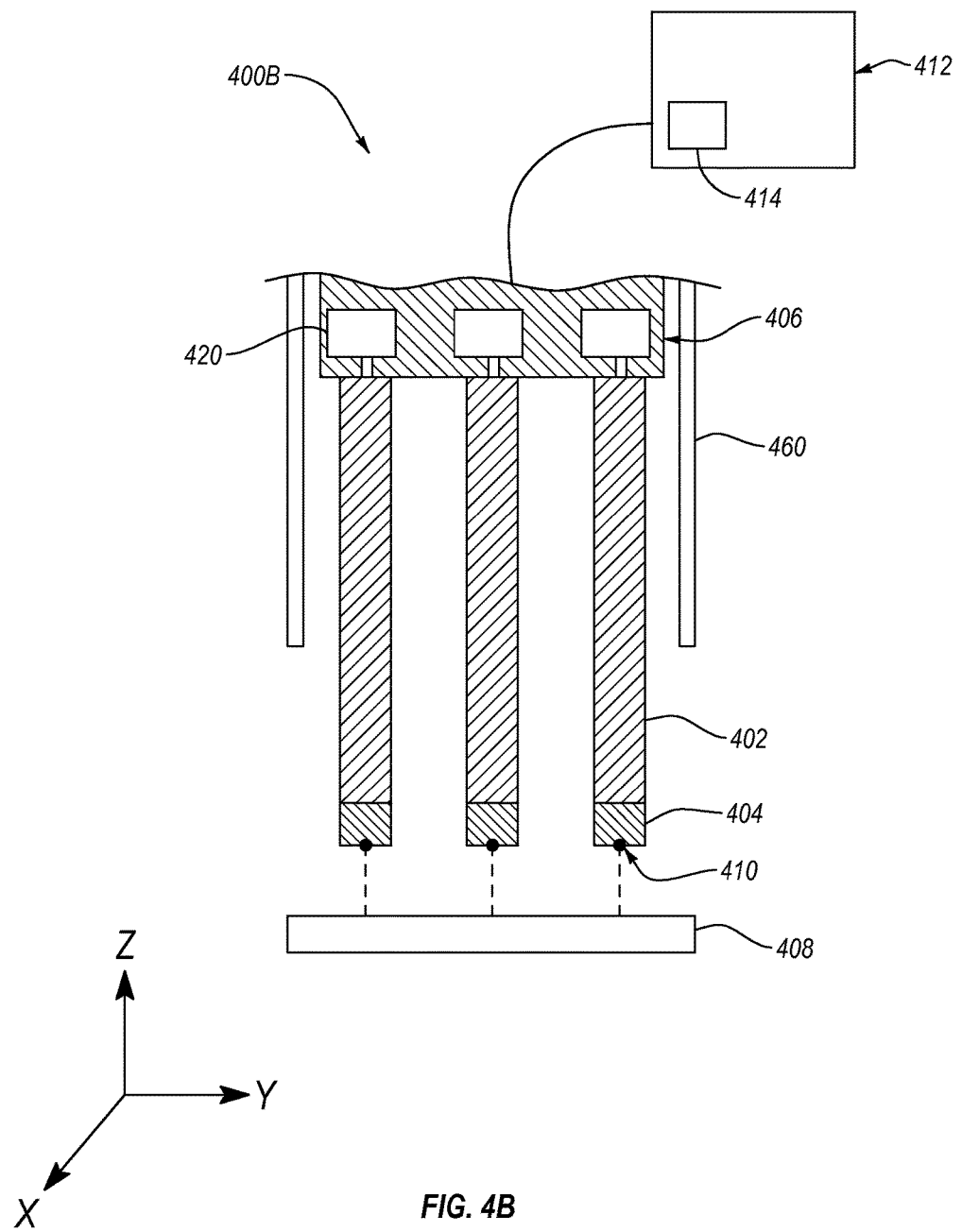
FIG. 4B is a schematic cross-sectional view of a printing system that is configured to be substantially inserted into an internal region of interest of a subject according to an embodiment.

FIGS. 4A and 4B are schematic cross-sectional views of different printing systems 400A and 400B each of which is configured to be inserted into an internal region of a body of a subject (e.g. during laparoscopic surgery), according to an embodiment. The printing systems 400A and 400B can utilize any of the printing system embodiments illustrated and described in connection with the printing systems shown in FIGS. 1-3D.

The printing systems 400A and 400B each include one or more steerable actuators 402 coupled to and support by the printing head 406. The one or more steerable actuators 402 can be coupled to one or more dispense elements 404. The one or more steerable actuators 402 can be controllably steered and the one or more dispense elements 404 can controllably dispense one or more materials responsive to a direction from the control electrical circuitry 414 of the controller 412. The controller 212 can be located remotely from the printing head 406.

Referring to FIG. 4A, the printing system 400A can be configured to only be partially inserted into an internal region of a living subject (e.g. an animal, a person). In such an embodiment, the printing head 406 can remain outside the subject while the one or more steerable actuators 402 can be configured to be inserted into the internal region (e.g., an epidermal region, an endodermal region, a subdermal region, a subcutaneous region, an intraperitoneal region, an intra-abdominal region, an intra-organ region, an intracranial region, a skeletal region, a muscular region, a nervous region, a cardiac region, a visceral region, a parietal region, a lumenal region, an endolumenal region, etc.). For example, during laparoscopic surgery, the printing head 406 can be positioned adjacent to an opening of a trocar or a cannula. The trocar or cannula can be partially inserted into the living subject. The one or more steerable actuators 402 can be inserted into the subject using the trocar or cannula.

The printing system 400A can include a body-insertable device 460 configured to subcutaneously insert the one or more steerable actuators 402 and one or more dispense elements 404 into the subject and access the region of interest 408. In an embodiment, the body-insertable device 460 can include a catheter, endoscope, or other suitable devices. For example, the body-insertable device 460 can include an endoscope that includes at least one channel configured to house the one or more steerable actuators 402 or the one or more dispense elements 404. The body-insertable device can be configured to protect or guide the one or more steerable actuators 402 and one or more dispense elements 404, while the one or more steerable actuators 402 and one or more dispense elements 404 are inserted into the subject. The body-insertable device 460 may also support the one or more steerable actuators 402 during the printing process. As such, the body-insertable device 460 can at least partially house the one or more steerable actuators 402 or the one or more dispense elements 404. For example, the portions of the one or more steerable actuators 402 and the one or more dispense elements 404 can protrude from the body-insertable device 460. Alternatively, the one or more steerable actuators 402 and the one or more dispense elements 404 can be configured to be completely housed in the body-insertable device 460 while being inserted into the subject. However, when the body-insertable device 460 is proximate the region of interest 408, the one or more steerable actuators 402 can actuate in the z-direction such that portions of the one or more steerable actuators 402 and the one or more dispense elements 404 protrude from the body-insertable device 460. In an embodiment, the body-insertable device 460 can be attached to the printing head 406. Alternatively, the body-insertable device 460 can only house a portion of the one or more steerable actuators 402 and the one or more dispense elements 404.

In an embodiment, the printing system 400A can be configured to operate during laparoscopic surgery. For example, the body-insertable device can at least partially house the one or more steerable actuators 402 and the one or more dispense elements 460. In such an embodiment, a trocar can be inserted into the subject and the body-insertable device 460 can be inserted into a subject via the trocar. An individual operating the printing system 400A can guide the body-insertable device 460 using one or more sensors 432 attached to the body-insertable device 460, the one or more steerable actuators 402, or the one or more dispense elements 404. The one or more sensors 432 can include a video camera with a cold light source (e.g., halogen or xenon). When the body-insertable device 460 reaches the region of interest 408, the control electrical circuitry 414 can controllably actuate the one or more steerable actuators 402 thereby controllably steering the one or more dispense elements 404. In an embodiment, the one or more dispense elements 404 can dispense one or more materials stored in the one or more material reservoirs 420 through at least one aperture 410 thereby printing an object on the region of interest 408.

In an embodiment, the printing system 400A can be used during the laparoscopic surgery. For example, the printing system 400A can print a medical implant. Similarly, the printing system 400A can print a scaffold including a medicament therein or thereon onto the region of interest 408 during or after the laparoscopic surgery. After the laparoscopic surgery is complete, the printing system 400A can be used to speed the healing process. For example, the printing system 400A can controllably dispense biological materials into the subject such as tissue, grafts, or cells, such as printing tissue, capillaries, or similar structures within the body. Such printing operations can facilitate faster healing of the wound. In an embodiment, the printing system 400A can only be configured to be used during or after the laparoscopic surgery.

FIG. 4B illustrates the printing system 400B that is substantially inserted subcutaneously into the subject, according to an embodiment. The printing system 400B can be substantially similar to the printing system 400A illustrated in FIG. 4A. However, the printing system 400B can include a body-insertable device 460 that can be configured to at least partially house the printing head 406 along with the one or more steerable actuators 402 and the one or more dispense elements 404. As such, the printing head 406 can be inserted subcutaneously into the subject along with the one or more steerable actuators 402 and the one or more dispense elements 404. However, the printing system 400B can be configured to be completely subcutaneously inserted without the use of the body-insertable device 460.

In the illustrated embodiment, the controller 412 is illustrated to be remote from the printing head 406 and configured to not be inserted subcutaneously into the subject. However, in other embodiments, the controller 412 can be configured to be inserted subcutaneously. For example, at least a portion of the controller 412 can be positioned within the printing head 406.

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer can opt for a mainly hardware and/or firmware vehicle; alternatively, if flexibility is paramount, the implementer can opt for a mainly software implementation; or, yet again alternatively, the implementer can opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which can vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In an embodiment, several portions of the subject matter described herein can be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electro-mechanical systems having a wide range of electrical components such as hardware, software, firmware, or virtually any combination thereof; and a wide range of components that can impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electrical systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context can dictate otherwise.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein can be implemented in an analog or digital fashion or some combination thereof.

This disclosure has been made with reference to various example embodiments. However, those skilled in the art will recognize that changes and modifications may be made to the embodiments without departing from the scope of the present disclosure. For example, various operational steps, as well as components for carrying out operational steps, may be implemented in alternate ways depending upon the particular application or in consideration of any number of cost functions associated with the operation of the system; e.g., one or more of the steps may be deleted, modified, or combined with other steps.

Additionally, as will be appreciated by one of ordinary skill in the art, principles of the present disclosure, including components, may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create a means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

In an embodiment, the printing systems disclosed herein can be integrated in such a manner that the printing systems operate as a unique system configured specifically for function of printing (e.g., three-dimensional printing), and any associated computing devices of the printing systems operate as specific use computers for purposes of the claimed system, and not general use computers. In an embodiment, at least one associated computing device of the printing systems operate as specific use computers for purposes of the claimed system, and not general use computers. In an embodiment, at least one of the associated computing devices of the printing systems are hardwired with a specific ROM to instruct the at least one computing device. In an embodiment, one of skill in the art recognizes that the printing devices and printing systems effects an improvement at least in the technological field of three-dimensional printing.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components can be referred to herein as "configured to." The reader will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, the recited operations therein can generally be performed in any order. Examples of such alternate orderings can include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A printing system, comprising:
   a printing head;
   one or more dispense elements, each of which includes at least one aperture, the one more dispense elements configured to controllably dispense one or more materials through the at least one aperture onto a region of interest;
   one or more steerable actuators exhibiting a longitudinal configuration, the one or more steerable actuators directly coupled to and extending longitudinally away from the printing head, the one or more steerable actuators operably coupled to the one or more dispense elements, the one or more steerable actuators configured to controllably steer the one or more dispense elements; and
   a controller including control electrical circuitry that is operably coupled to the printing head, the one or more dispense elements and the one or more steerable actuators, the control electrical circuitry configured to direct actuation of the one or more steerable actuators and dispensing of the one or more materials from the one or more dispense elements.

2. The printing system of claim 1, wherein the one or more steerable actuators include at least one of a pneumatic actuator, a hydraulic actuator, a piezoelectric actuator, a shape memory material actuator, or an electroactive polymer actuator.

3. The printing system of claim 1, wherein the one or more steerable actuators are configured to controllably steer the one or more dispense elements in two or more directions.

4. The printing system of claim 1, wherein the one or more dispense elements include a plurality of dispense elements, wherein at least one of the plurality of dispense elements is configured to dispense a first material and at least another of the plurality of dispense elements is configured to dispense a second material that is different than the first material.

5. The printing system of claim 1, wherein the one or more dispense elements include at least one of one or more microconduits configured to allow the one or more materials to flow therethrough, one or more nozzles configured to dispense the one or more materials, or one or more tubes configured to allow the one or more material to flow therethrough.

6. The printing system of claim 1, wherein each of the one or more steerable actuators and the one or more dispense elements is configured to operate in at least one of ex vivo, in vivo, or in vitro environment.

7. The printing system of claim 1, wherein the one or more dispense elements includes a plurality of dispense elements, and wherein the one or more steerable actuators include a plurality of actuators each of which is operably coupled to a corresponding one of the plurality of dispense elements and independently actuated by the controller.

8. The printing system of claim 1, wherein the printing head is moveable to position the one or more dispense elements under direction from the control electrical circuitry of the controller.

9. The printing system of claim 8, wherein the printing head is configured to remain substantially stationary while the one or more dispense elements dispense the one or more materials.

10. The printing system of claim 1, further including one or more material reservoirs storing the one or more materials, the one or more material reservoirs fluidly coupled to the one or more dispense elements to provide the one or more materials thereto.

11. The printing system of claim 10, wherein the one or more material reservoirs are fluidly coupled to the one or more dispense elements via one or more conduits through which the one or more materials can flow.

12. The printing system of claim 10, wherein the one or more materials stored by the one or more material reservoirs include at least one of metallic material, ceramic material, conductive material, organic material, or non-organic material.

13. The printing system of claim 10, wherein the one or more materials stored by the one or more material reservoirs include one or more biomaterials.

14. The printing system of claim 13, wherein the one or more biomaterials include biomaterials suitable to form at least one of implants, grafts, or tissues.

15. The printing system of claim 13, wherein the one or more biomaterials include one or more cells.

16. The printing system of claim 15, wherein the one or more cells include one or more transfected cells.

17. The printing system of claim 10, wherein the one or more materials are encapsulated.

18. The printing system of claim 1, further including one or more sensors configured to sense at least one characteristic about the region of interest.

19. The printing system of claim 18, wherein the at least one characteristic includes temperature, pressure, hydration, or chemistry of the region of interest.

20. The printing system of claim 18, wherein the one or more sensors are mounted to the printing head.

21. The printing system of claim 18, wherein the one or more sensors are positioned to not influence the dispensing of the one or more materials from the one or more dispense elements.

22. The printing system of claim 18 wherein the one or more sensors include at least one of a pressure sensor, a temperature sensor, biosensor, a chemical sensor, a hydration sensor, a position sensor, a depth sensor, an optical sensor, an acoustic sensor, or an infrared sensor.

23. The printing system of claim 18, further including one or more flexible elongated members to which the one or more dispense elements are mounted, wherein the one or more sensors are mounted to or near the one or more flexible elongated members.

24. The printing system of claim 23, wherein the one or more dispense elements are the flexible elongated members.

25. The printing system of claim 1, wherein the one or more dispense elements are remotely located from the controller.

26. The printing system of claim 1, wherein the controller includes a user interface configured to enable a user to input at least one of commands or instructions for operating the one or more steerable actuators and the one or more dispense elements.

27. The printing system of claim 1, wherein the controller includes memory storing operational instructions for operating the one or more dispense elements and the one or more steerable actuators, and one or more processors configured to direct operation of the one or more dispense elements and the one or more steerable actuators based on the operational instructions.

28. The printing system of claim 1, wherein the one or more steerable actuators are reversibly attached to the printing head.

29. A printing system, comprising:
a body-insertable device configured to be inserted into a subject to access an internal region of interest therein;
a printing head that is distinct from the body-insertable device;
one or more dispense elements, each of which includes at least one aperture, the one or more dispense elements configured to controllably dispense one or more materials through the at least one aperture onto the internal region of interest;
one or more steerable actuators exhibiting a longitudinal configuration, the one or more steerable actuators directly coupled to the one or more dispense elements and extending longitudinally away from the printing head, the one or more steerable actuators configured to controllably steer the one or more dispense elements, the one or more steerable actuators at least partially positioned within the body-insertable device; and
a controller including control electrical circuitry that is operably coupled to the one or more dispense elements and the one or more steerable actuators, the control electrical circuitry configured to direct actuation of the one or more steerable actuators and dispense of the one or more materials from the one or more dispense elements.

30. The printing system of claim 29, wherein the body-insertable device houses the one or more dispense elements and the one or more steerable actuators.

31. The printing system of claim 29, wherein the body-insertable device includes an endoscope having at least one channel that houses the one or more dispense elements or the one or more steerable actuators.

32. The printing system of claim 29, wherein the controller is remotely located from the body-insertable device, the one or more dispense elements, and the one or more steerable actuators.

33. The printing system of claim 29, wherein the one or more dispense elements are operably coupled to the printing head, the printing head operably coupled to the controller and being moveable to position the one or more dispense elements under direction from the control electrical circuitry.

34. The printing system of claim 33, further including one or more sensors configured to sense at least one characteristic about the region of interest.

35. The printing system of claim 34, wherein the at least one characteristic includes temperature, pressure, hydration, or chemistry of the region of interest.

36. The printing system of claim 33, wherein the one or more sensors are mounted to the body-insertable device, the one or more dispense elements, the one or more steerable actuators, or the printing head.

37. The printing system of claim 29, further including one or more sensors configured to sense at least one characteristic about the region of interest.

38. The printing system of claim 29, wherein the internal region of interest includes an epidermal region, an endodermal region, a subdermal region, a subcutaneous region, an intraperitoneal region, an intra-abdominal region, an intra-organ region, an intracranial region, a skeletal region, a muscular region, a nervous region, a cardiac region, a lumenal region, an endolumenal region, a wound site, or a surgical site.

39. The printing system of claim 1, wherein the one or more dispense elements are directly coupled to or integrally formed with the one or more steerable actuators, the one or more steerable actuators positioned to space the one or more dispense elements from the printing head.

40. The printing system of claim 1, wherein the one or more steerable actuators include an interfacial surface that is remote from the printing head and at least one external lateral surface extending longitudinally away from the printing head to the interfacial surface.

41. The printing system of claim 10, wherein the one or more material reservoirs are disposed in the printing head.

42. The printing system of claim 10, further comprising one or more conduits extending from the one or more material reservoirs to the one or more dispense elements.

* * * * *